(12) United States Patent
Le et al.

(10) Patent No.: US 10,709,797 B2
(45) Date of Patent: Jul. 14, 2020

(54) ISOLATION OF EXTRACELLULAR VESICLES (EVS) FROM RED BLOOD CELLS FOR GENE THERAPY

(71) Applicant: City University of Hong Kong, Kowloon (HK)

(72) Inventors: Thi Nguyet Minh Le, Kowloon (HK); Jiahai Shi, Kowloon (HK); Muhammad Waqas, Karachi (PK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 73 days.

(21) Appl. No.: 15/678,363

(22) Filed: Aug. 16, 2017

(65) Prior Publication Data

US 2019/0054192 A1 Feb. 21, 2019

(51) Int. Cl.

| C12N 15/11 | (2006.01) |
|---|---|
| A61K 48/00 | (2006.01) |
| C07H 21/02 | (2006.01) |
| C07H 21/04 | (2006.01) |
| C12N 15/90 | (2006.01) |
| C12N 9/22 | (2006.01) |
| A61K 35/13 | (2015.01) |
| A61K 35/14 | (2015.01) |
| G01N 33/49 | (2006.01) |
| C12N 15/88 | (2006.01) |

(Continued)

(52) U.S. Cl.
CPC .......... *A61K 48/0075* (2013.01); *A61K 35/13* (2013.01); *A61K 35/14* (2013.01); *A61K 48/005* (2013.01); *A61K 48/0008* (2013.01); *A61K 48/0041* (2013.01); *A61K 48/0091* (2013.01); *C12N 5/0641* (2013.01); *C12N 9/22* (2013.01); *C12N 15/88* (2013.01); *C12N 15/907* (2013.01); *G01N 33/491* (2013.01); *A61K 35/00* (2013.01); *A61K 2035/128* (2013.01); *C12N 2310/11* (2013.01); *C12N 2310/122* (2013.01); *C12N 2310/20* (2017.05)

(58) Field of Classification Search
CPC ............ A61K 48/0041; A61K 48/0075; A61K 35/13; A61K 35/14; C12N 9/22
See application file for complete search history.

(56) References Cited

U.S. PATENT DOCUMENTS

| 9,085,778 B2 | 7/2015 | Lotvall et al. |
|---|---|---|
| 9,629,929 B2 | 4/2017 | Lotvall |
| 2009/0274630 A1 | 11/2009 | Huang |

FOREIGN PATENT DOCUMENTS

| RU | 2608509 C1 | 1/2017 |
|---|---|---|
| WO | 2016187717 | 12/2016 |

(Continued)

OTHER PUBLICATIONS

Chang et al. (Nanotechonology, 2010 vol. 21:1-9).*

(Continued)

*Primary Examiner* — Terra C Gibbs
(74) *Attorney, Agent, or Firm* — Renner Kenner Greive Bobak Taylor & Weber

(57) ABSTRACT

A method of RNA delivery using extracellular vesicles (EVs) derived from red blood cells (RBCs). The method comprises the purification and electroporation of the EVs and applying the RNA-loaded EVs to target cells. The method further comprises the treatment of cancer using the RNA-loaded EVs.

24 Claims, 23 Drawing Sheets

Specification includes a Sequence Listing.

(51) Int. Cl.
  *C12N 5/078* (2010.01)
  *A61K 35/12* (2015.01)
  *A61K 35/00* (2006.01)

(56) References Cited

FOREIGN PATENT DOCUMENTS

| WO | WO2017/054085 | 4/2017 |
|---|---|---|
| WO | 2018062973 | 4/2018 |

OTHER PUBLICATIONS

Vader et al. (Ther. Deliv. (2014) vol. 5:105-107).*
Zhang et al. (Molecular Cancer, 2011 vol. 10:1-13).*
Sunkara et al. (Analyst, first published on Oct. 26, 2015, vol. 141:371-381).*
Raimondo et al. (Abstract PW4.11, The Fifth International Meeting of ISEV, May 4, 2016).*
Alvarez-Erviti et al. (Nature Biotechnology, 2011 vol. 29:341-345, plus online material).*
Usman et al. (Nat Commun. Jun. 15, 2018;9(1), including Supplementary Information and Peer Review File).*
Zhang et al. (Intechopen, Books—Erythrocyte, published Nov. 15, 2018) downloaded from https://www.intechopen.com/books/erythrocyte/the-biology-and-therapeutic-applications-of-red-blood-cell-extracellular-vesicles on Mar. 20, 2020.*
Duc Bach Nguyen, Thi Bich Thuy Ly and Ingolf Bernhardt (Jul. 12, 2017). Microvesicles Released from Human Red Blood Cells: Properties and Potential Applications, Novel Implications of Exosomes in Diagnosis and Treatment of Cancer and Infectious Diseases, Jin Wang, IntechOpen, DOI: 10.5772/intechopen.69599.
Nguyen et al., Characterization of microvesicles released from human red blood cells. Cellular Physiology and Biochemistry, 2016; 38:1085-1099.
Daniel Xin Zhang, Theodoros Kiomourtzis, Chun Kuen Lam and Minh T.N. Le (Nov. 5, 2018). The Biology and Therapeutic Applications of Red Blood Cell Extracellular Vesicles [Online First], IntechOpen, DOI: 105772/intechopen.81758.
Alvarez-Erviti, L et al. "Delivery of siRNA to the mouse brain by systemic injection of targeted exosomes" Nature Biotechnology, vol. 29, No. 4 (Apr. 2011) p. 341-345. Submitted with Supplemental Information.
Wahlgren, J et al., "Plasma exosomes can deliver exogenous short interfering RNA to monocytes and lymphocytes" Nucleic Acids Research, 2012, vol. 40, No. 17 e130 doi:10.1093/nar/gks463 pp. 1-12.
Kooijmans, Sander A.A. et al., "Electroporation-induced siRNA precipitation obscures the efficiency of siRNA loading into extracellular vesicles" Journal of Controlled Release 172 (2013) 229-238.

\* cited by examiner

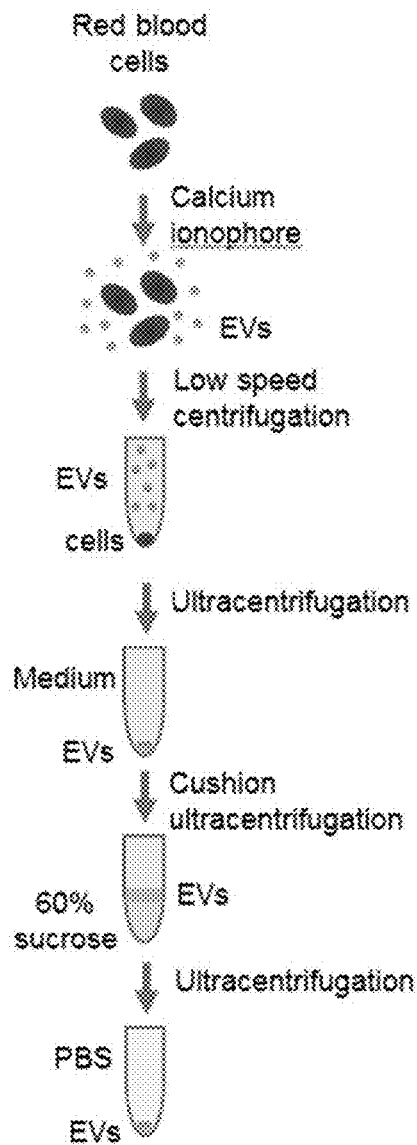
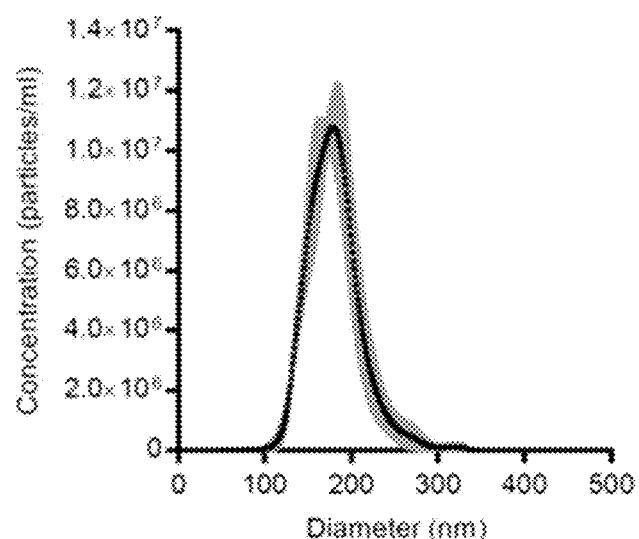
Figure 1b
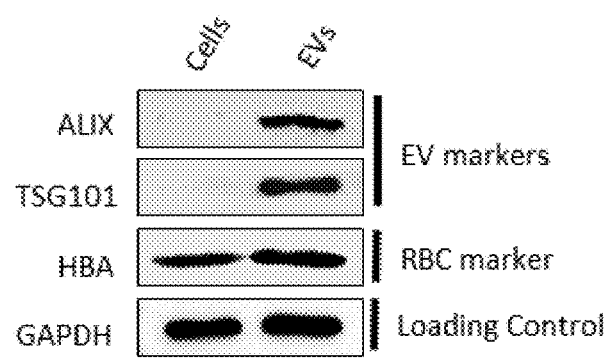
Figure 1c
Figure 1a

ISOLATION OF EXTRACELLULAR VESICLES (EVS) FROM RED BLOOD CELLS FOR GENE THERAPY

SEQUENCE LISTING

The Sequence Listing file entitled "sequencelisting" having a size of 6,395 bytes and a creation date of Aug. 16, 2017, that was filed with the patent application is incorporated herein by reference in its entirety.

FIELD OF INVENTION

The present invention relates to the field of molecular biology and genome editing, more specifically the transfer of genetic materials to recipient cells by extracellular vesicles (EVs).

BACKGROUND

RNA therapeutics including antisense oligo nucleotides (ASOs), small-interfering RNA (siRNAs), synthetic mRNAs and genome editing RNA-protein complexes are emerging as new modalities for therapies targeting the human genomes at high specificity and great flexibility. ASOs and siRNAs have been widely used as the tools for gene knockdown in biomedical research. Their ability to silence any gene of interest offers a great potential for targeting disease-prevalent genes. Various chemical modifications or conjugations can be used to keep ASOs and siRNAs stable and enhance their binding specificity. Common methods for RNA transfection including nucleofection, lipofection and electroporation are only suitable for ex vivo delivery. Viral transduction and nanoparticles are often used for in vivo delivery of RNAs and DNAs however, these methods are usually ineffective, immunogenic and toxic.

One of the most recent breakthroughs in Science is a new technology for genome editing, the clustered regularly interspaced short palindromic repeats (CRISPR) method that enables robust and precise modifications of genomic DNA for a wide range of applications in research and medicine. CRISPR is an ideal tool for correction of genetic abnormalities in cancer as the system can be designed to target genomic DNA directly. A CRISPR system involves two main components: a Cas9 enzyme and a guide (gRNA). The gRNA contains a targeting sequence for DNA binding and a scaffold sequence for Cas9 binding. Cas9 nuclease is often used to "knockout" target genes hence it can be applied for deletion or suppression of oncogenes that are essential for cancer initiation or progression. Similar to ASOs and siRNAs, the CRISPR system offers a great flexibility in targeting any gene of interest hence, potential CRISPR based therapies can be designed based on the genetic mutation in individual patients. An advantage of the CRISPR system is its ability to completely ablate the expression of disease genes which can only be suppressed partially by RNA interference methods with ASOs or siRNAs. Furthermore, multiple gRNAs can be employed to suppress or activate multiple genes simultaneously, hence increasing the treatment efficacy and reducing resistance potentially caused by new mutations in the target genes. The applications of CRISPR technology have evolved very quickly from bench to bedside targeting different diseases. Clinical trials of CRISPR-mediated modification of T cells for cancer therapies have started in China and in the USA. Many other CRISPR-based therapies are under development. However, most of these therapies rely on ex vivo modification of the target cells or systemic delivery of the CRISPR system using virus or nanoparticles that can target very few cell types such as hepatocytes.

Acute myeloid leukemia (AML) is the most aggressive type of blood cancer that affects nearly 352,000 people per year with the 5-year prevalence of 1.5%. AML is characterized by the increase of myeloblasts in the peripheral blood (PB) and the bone marrow (BM). 30-40% AML patients (mostly under 60 years old) response well to chemotherapy and hematopoietic stem cell transplantation. However, the response rate is much lower in older patients as they cannot tolerate the toxicity of chemotherapy. Moreover, almost all the patients relapse after a certain time due to drug resistance. Hence, new treatment strategies are desirable to increase the response rate, reduce toxicity and combat drug resistance. Recent advances in genomics have provided better understanding of the genetic and epigenetic abnormalities in AML and suggest new specific therapeutic targets. RNA interference and genome editing methods are emerging as new approaches to target these abnormalities. However, delivery of RNAs to AML cells for gene therapies has proven challenging, especially for in vivo treatments. Common gene therapy delivery vehicles such as adeno-associated virus (AAV) and lipid nanoparticles (LNPs) are mostly ineffective or toxic in AML models.

Therefore, there is a desire to improve the delivery efficiency and reduce toxicity of gene therapies for cancer.

SUMMARY OF INVENTION

In one aspect of the invention, there is provided a method for RNA delivery to target cells comprising the steps of: a) purification of extracellular vesicles (EVs) from red blood cells (RBCs); b) electroporation of the EVs with RNAs to form RNA-loaded EVs; and c) applying the RNA-loaded EVs to the target cells.

The advantage of using EVs (including microvesicles and exosomes) from RBCs is that the RBCs are the most abundant blood cells hence a large amount of EVs can be obtained and purified from RBC units that are available at any blood bank. Preferably, the RBCs are derived from a human. They are also nontoxic, unlike synthetic transfection reagents. RBC EVs do not contain oncogenic DNA/RNA or growth factors that are usually abundant in EVs from cancer cells or stem cells, hence RBC EVs do not post any transformation risks to recipient cells.

In one embodiment, the RBCs are derived from a mammal preferably a human and treated with ionophore in particular calcium ionophore. The EVs are purified using ultracentrifugation with a sucrose cushion. The term "sucrose cushion" refers to a sucrose gradient which establishes itself during a centrifugation. In an embodiment, the sucrose gradient is prepared by using a solution of about 40% to about 70%, about 50% to about 60%, or about 60% of sucrose.

In another embodiment, the electroporated EVs comprises antisense oligonucleotides (ASO), mRNAs and plasmids. Preferably, the ASO comprises or consists of SEQ ID NO: 1.

In a further embodiment, the target cells comprise cancer cells, or are cancer cells. In another embodiment, the target cells comprise leukemia cells in particular acute myeloid leukemia (AML) cells, breast cancer cells, or a combination of AML cells and breast cancer cells.

In another embodiment, the EVs are electroporated with ASO antagonizing miR-125b for knockdown of miR-125b in target cells as described above. Preferably, the ASO antagonizing miR-125b comprises or consists of SEQ ID NO: 1.

In another embodiment, the growth of the target cells is suppressed. In a further embodiment, the EVs are electroporated with a small chemical such as dextran.

In another embodiment, the method comprises administering to the target cells the RNA-loaded EVs which modulate an apoptosis-related gene expression, thereby inducing apoptosis in the target cells.

In a second aspect of the invention, there is provided a method for delivery of an antisense oligonucleotide (ASO) to target cells to suppress gene expression, comprising the steps of: a) purification of extracellular vesicles (EVs) from red blood cells (RBCs); b) electroporation of the EVs with RNAs to form RNA-loaded EVs; and c) applying the RNA-loaded EVs to the target cells.

In an embodiment, as described above, the RBCs are derived from a mammal preferably a human, and treated with ionophore in particular calcium ionophore.

In one embodiment, the RNA is an ASO antagonizing miR-125b to inhibit the oncogenic miR-125b in the target cells. Preferably, the ASO antagonizing miR-125b comprises or consists of SEQ ID NO: 1.

In another embodiment, the target cells comprise cancer cells or are cancer cells. In another embodiment, the target cells comprise leukemia cells in particular AML cells, breast cancer cells, or a combination of AML cells and breast cancer cells.

In a third aspect of the invention, there is provided a method of RNA delivery to target cells for a CRISPR genome editing system comprising the steps of: a) purification of extracellular vesicles (EVs) from red blood cells (RBCs), wherein the RBCs are preferably derived from a human and treated with ionophore in particular calcium ionophore; b) electroporation of the EVs with RNAs which may be Cas9 mRNAs and/or gRNAs to form RNA-loaded EVs; and c) applying the RNA-loaded EVs to the target cells. CRISPR is a method that enables robust and precise modifications of genomic DNA for a wide range of applications in research and medicine. The system can be designed to target genomic DNA directly.

In one embodiment, the EVs are electroporated with Cas9 mRNA and gRNA. Preferably, Cas9 mRNA comprises or consists of SEQ ID NO: 2. Further, the gRNA is eGFP gRNA comprising or consisting of SEQ ID NO: 3.

In another embodiment, the EVs are electroporated with Cas9 and gRNA plasmids. In another embodiment, the target cells comprise cancer cells or are cancer cells.

In a further embodiment, the target cells comprise leukemia cells or are leukemia cells. In a particular embodiment, the target cells comprise leukemia cells in particular AML cells, breast cancer cells, or a combination of AML cells and breast cancer cells.

In a fourth aspect of the invention, there is provided a method of treating cancer by delivery of RNA to target cells comprising the steps of: a) purification of extracellular vesicles (EVs) from red blood cells (RBCs) which are preferably derived from a mammal in particular a human and treated with ionophore in particular calcium ionophore; b) electroporation of the EVs with RNAs to form RNA-loaded EVs; and c) applying the RNA-loaded EVs to the target cells thereby inhibiting the growth of the target cells, wherein the target cells comprise cancer cells.

In one embodiment, the target cells comprise leukemia cells, breast cancer cells, or a combination of leukemia cells and breast cancer cells. In another embodiment, the target cells comprise acute myeloid leukemia cells.

In another embodiment, the step c) comprises a step of administering the RNA-loaded EVs to a subject having the target cells via a local or systemic administration. Local administration refers to the delivery of the RNA-loaded EVs directly to the site of action, and includes, but not limiting to, intratumoral administration. Systemic administration refers to the delivery of the RNA-loaded EVs via circulatory system, and includes, but not limiting to, intravenous injection.

In a further embodiment, the growth of the target cells is suppressed after the step c).

BRIEF DESCRIPTION OF THE DRAWINGS

FIG. 1a is a schematic diagram showing the process of collecting the Evs from human red blood cells (RBCs). FIG. 1b is a plot showing the concentration and the size distribution of RBC EVs. FIG. 1c shows the expression of ALIX, TSG101, and hemoglobin A in cell lysates and EVs, via Western blot analysis.

DETAILED DESCRIPTION OF THE INVENTION

Figure 2A:
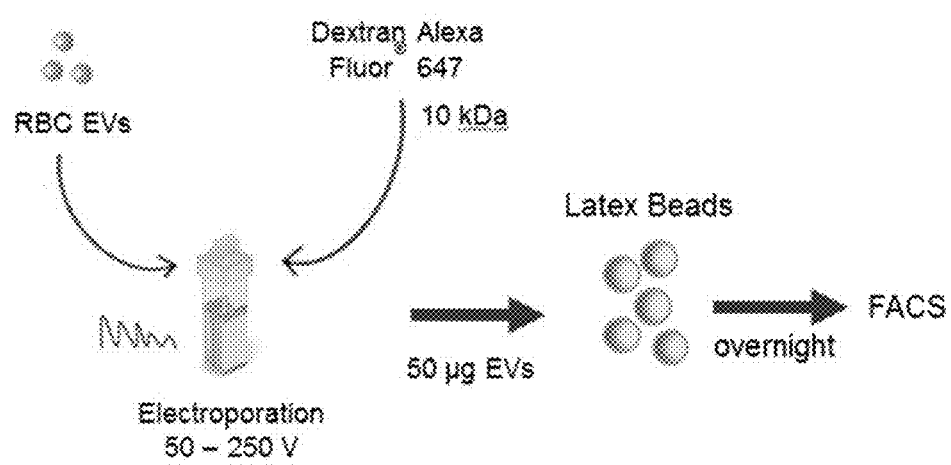
FIG. 2a is a schematic presentation of EV electroporation.

The present invention relates to the field of molecular biology and genome editing. More specifically the transfer of genetic materials to recipient cells by extracellular vesicles (EVs) and the method of purification or isolation of exosomes from Red Blood Cells.

Cells release into the extracellular environment, diverse types of membrane vesicles of endosomal and plasma membrane origin, called exosomes and microvesicles, respectively. These extracellular vesicles (EVs) represent an important mode of intercellular communication by serving as vehicles for transfer between cells of membrane and cytosolic proteins, lipids, and RNA.

EVs secreted by many cell types contain RNAs that function to alter the phenotypes of other cells. EVs contain not only RNAs but also proteins that stabilize RNAs and facilitate the functions of RNAs in the target cells.

EV-mediated delivery of RNAs is an attractive platform because the natural biocompatibility of EVs is the solution to overcome most in vivo delivery hurdles. EVs are generally nontoxic and non-immunogenic. They are taken up readily by many cell types but they do possess some antiphagocytic markers such as CD47 that help them to evade the phagocytosis by macrophages of the reticuloendothelial system. Moreover, EVs are able to extravasate well through the interendothelial junctions and even cross the blood-brain barrier hence, they are greatly versatile drug carriers. Of clinical value, delivery by EVs is not hampered by the multidrug resistance mechanism caused by overexpression of P-glycoproteins that tumor cells often exhibit to eliminate many chemical compounds.

For therapeutic delivery, many research groups have attempted to produce EVs from cancer cell lines and stem cells which are very costly due to the large-scale cell culture that requires various supplements. Moreover, EVs from cancer and stem cells may contain oncogenic proteins or growth factors that promote cancer growth. EVs from plasma and blood cells are safer for cancer therapies. RBCs EVs do not contain oncogenic DNA/RNA or growth factors that are usually abundant in EVs from cancer cells or stem cells, hence, RBC EVs do not post any transformation risks to recipient cells. RBCs EVs are also nontoxic unlike synthetic transfection reagents. A recent article by Wahlgren et al describes a protocol for isolation of plasma exosomes, small EVs that are derived from multivesicular bodies, and electroporation of these exosomes with siRNAs. They demonstrated that siRNA-loaded exosomes are taken up by monocytes and lymphocytes leading to significant knockdown of the target genes. This method is probably applicable to cancer therapies however, plasma exosomes are normally very heterogeneous because they are derived from different cell types in the circulation and the yield of exosomes from plasma is low. RBCs on the other hand are homogenous as RBCs from each individual are the same.

In the present invention, an RNA is selected to inhibit expression of a target gene by binding to a miRNA or editing the target genomic DNA. Further, there is provided a novel method for the purification of EVs from red blood cells (RBCs) and incorporation of RNAs in EVs for gene therapies against cancer, including acute myeloid leukemia and breast cancer.

EXAMPLES

The present invention is described by reference to the following Examples, which are offered by way of illustration and are not intended to limit the invention in any manner.

Example 1

Materials and Methods

Blood samples were obtained by Red Cross from healthy donors in Hong Kong with informed consents. RBCs were separated from plasma and white blood cells by centrifugation and treated with 10 mM calcium ionophore (Sigma) overnight. The purification of EVs were optimized with multiple centrifugation steps including the removal of protein contamination using a 60% sucrose cushion (ultracentrifugation at 100,000×g) that yields a homogenous population of EVs with an average diameter of ~140 nm. Each unit of RBCs, isolated from ~300 ml blood, yield 7.1 mg EVs on average. These EVs are enriched in EV markers, ALIX and TSG101, as shown by Western blot analysis. They also contain hemoglobin A which is a major protein from RBCs.

FIG. 1a: Culture supernatants were collected from ionophore-treated human red blood cells and subjected to multiple steps of centrifugation to remove dead cells and debris. EVs were purified by ultracentrifugation with 60% sucrose cushion and washed with phosphate buffer saline (PBS) by ultracentrifugation (100,000×g). FIG. 1b: Concentrations and the size distribution of RBC EVs were measured by a Nanosight nanoparticle analyzer. FIG. 1c: Western blot analysis of ALIX, TSG101 (EV markers) and Hemoglobin A (RBC marker) relative to GAPDH in the cell lysate and EVs purified from RBCs.

Subsequently, an electroporation protocol was optimized for the RBC EVs using Dextran conjugated with Alexa Fluor® 647 (AF647, Thermo Fisher Scientific) tested at different voltages using a Gene Pulser Xcell electroporator (BioRad). Electroporated EVs were added to latex beads and analyzed for AF647 using flow cytometry. It was found that 250 V was the optimal voltage, which resulted in 93.6% AF647 positive EV-bound beads.

Figure 2B:
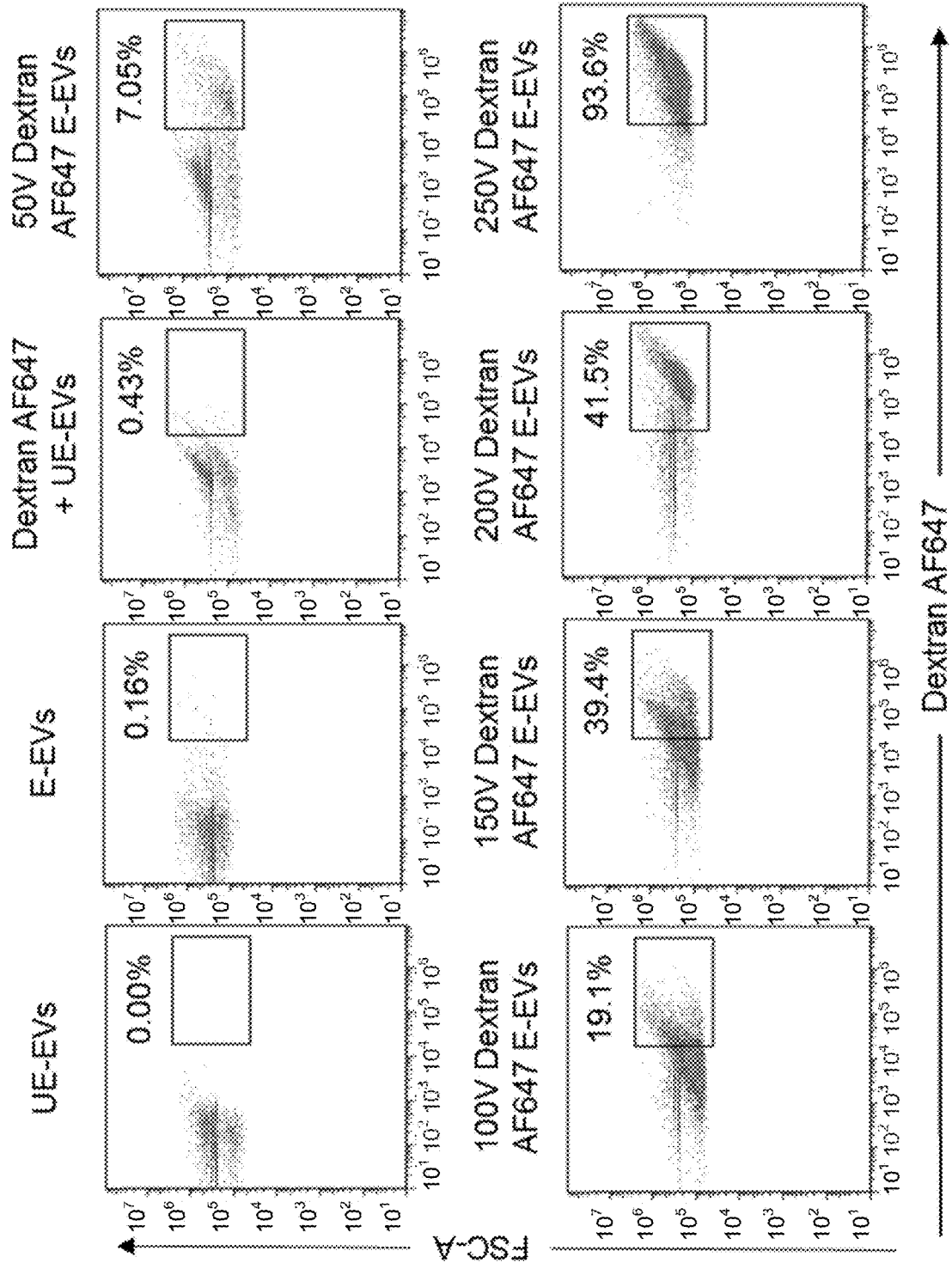
FIG. 2b show the results obtained from FACS analysis of AF647 fluorescence and forward scatter (FSC) of the beads that were incubated with electroporated EVs (E-EVs) or unelectroporated EVs (UE-EVs).

FIG. 2a: Schematic presentation of EV electroporation: 50 μg RBC EVs were mixed with 4 μg Alexa Fluor® 647 (AF647) labeled Dextran and electroporated at different voltages from 50 to 250 V. EVs were incubated with latex beads overnight and analyzed by fluorescent activated cell sorting (FACS). FIG. 2b: FACS analysis of AF647 fluorescence and forward scatter (FSC) of the beads that were incubated with electroporated EVs (E-EVs) or unelectroporated EVs (UE-EVs). The percentage of AF647 positive beads are indicated above the gates.

To measure the uptake of EVs by AML cells, the RBC-derived EVs was labelled with a fluorescent membrane dye called Bodipy® TR (Thermo Fisher). Labeled EVs were washed extensively using the sucrose cushion, mock electroporated and added to the AML MOLM13 cells. After 24 hours of incubation with EVs, Western blot analysis of MOML13 cells showed a clear uptake of Hemoglobin A (HBA) protein which was absent in the untreated cells. Importantly, treatment with RBC EVs did not affect the viability of AML cells as shown by FACS analysis. MOLM13 cells became 100% Bodipy positive after the incubation with Bodipy-labeled EVs, indicating that all the cells took up the fluorescent RBC EVs. Electroporation increased the uptake of HBA but not Bodipy by MOLM13 cells.

Figure 3A:
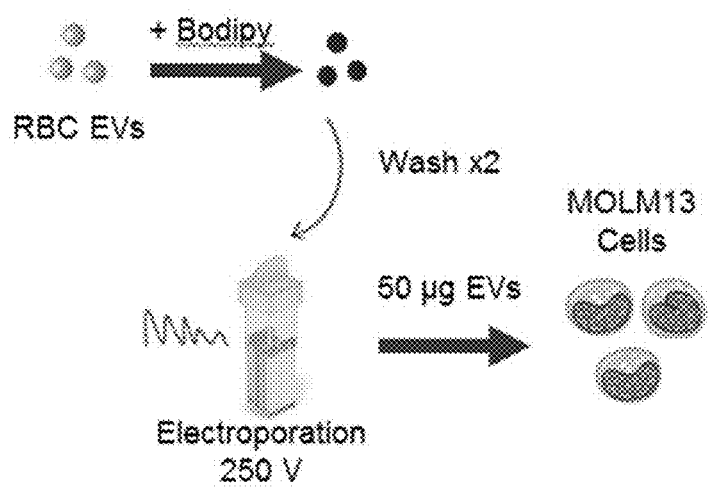
FIG. 3a is a schematic presentation of the EV uptake assay.
Figure 3B:
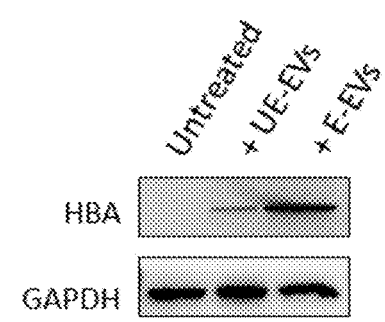
FIG. 3b shows the expression of HBA relative to GAPDH, via Western blot analysis.
Figure 3C:
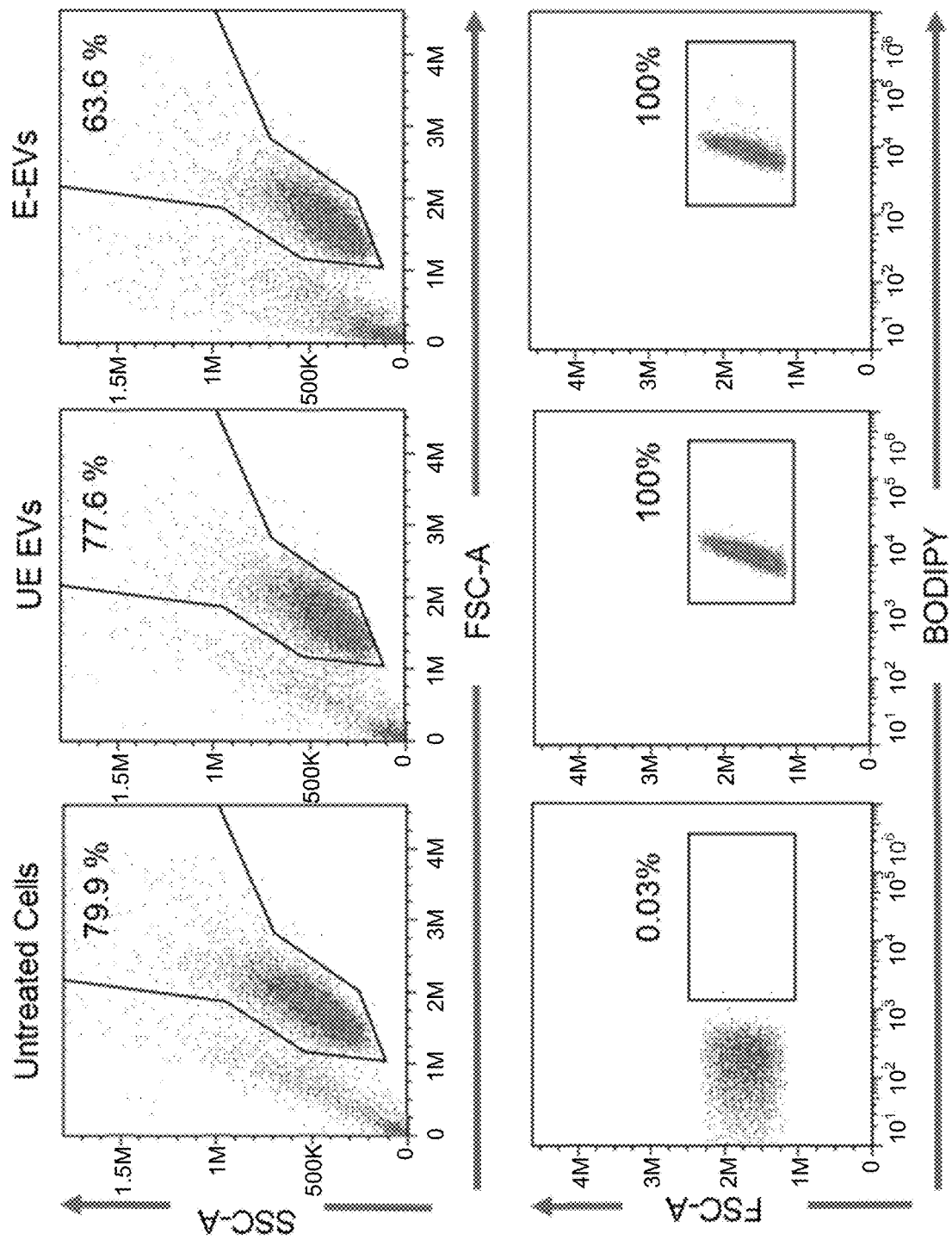
FIG. 3c shows the uptake of RBC EVs by leukemia MOLM13 cells, via FACS analysis.

FIG. 3a: Schematic presentation of the EV uptake assay: 50 μg RBC EVs were labeled with Bodipy TR (a red fluorescent dye), washed twice, mock electroporated at 250 V, and incubated with MOLM13 cells for 24 hours. FIG. 3b: Western blot analysis of hemoglobin A (HBA) relative to GAPDH and; FIG. 3c: FACS analysis of live cells, gated based on size scatter (SSC) and forward scatter (FSC), and BODIPY fluorescence in MOLM13 cells that were untreated or incubated with electroporated EVs (E-EVs) or unelectroporated EVs (UE-EVs).

Different amounts of EVs was further electroporated with Dextran AF647 and it was found that the best delivery with 75 μg EVs resulted in 68.6% cells positive for AF647. Therefore, 75 μg EVs was used for subsequent experiments.

Figure 4A:
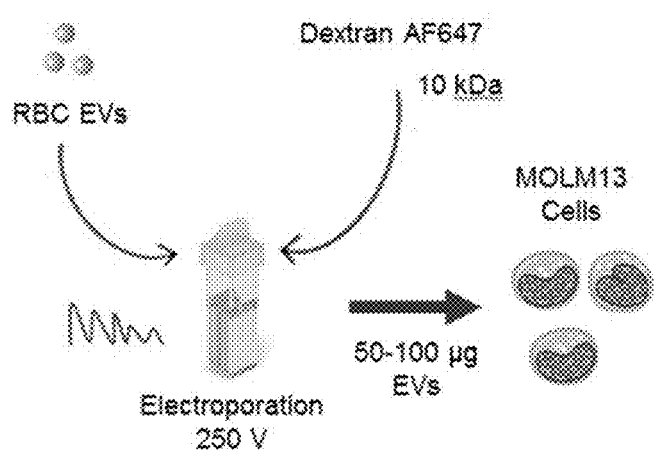
FIG. 4a is a schematic presentation of Dextran delivery.
Figure 4B:
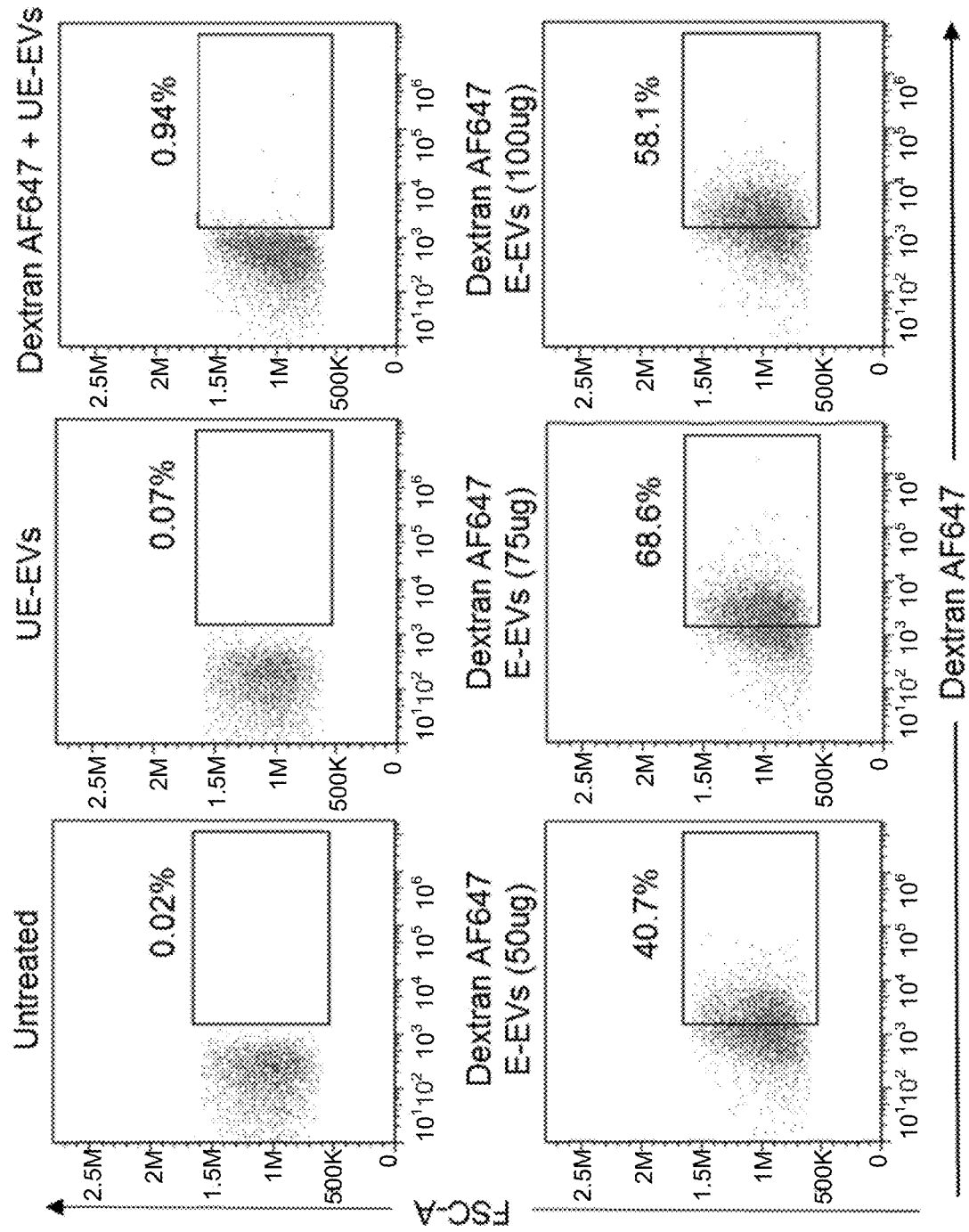
FIG. 4b shows RBC EVs deliver dextran to leukemia MOLM13 cells, via FACS analysis.

FIG. 4a: Schematic presentation of Dextran delivery: 50-100 μg RBC EVs were mixed with 4 μg Dextran AF647 and electroporated at 250 V. Electroporated EVs were incubated with MOLM13 cells for 24 hours. FIG. 4b: FACS analysis of Dextran AF647 fluorescence in MOLM13 cells that were untreated or incubated with 50-100 μg Dextran AF647 electroporated EVs (E-EVs) or 100 μg unelectroporated (UE-EVs).

Testing the delivery of RNA was started with an FAM (green fluorescent) labeled scrambled RNA oligonucleotide (Shanghai GenePharma), about 7 kDa, that is often used as a negative control antisense oligonucleotide (ASO). RBC EVs were electroporated with the FAM ASO and incubated with MOLM13 cells. After 24 hours, it was observed that ~70% uptake of FAM ASO by MOLM13 cells. Similar uptake was observed in NOMO-1 cells, another AML cell line (data not shown).

Figure 5A:
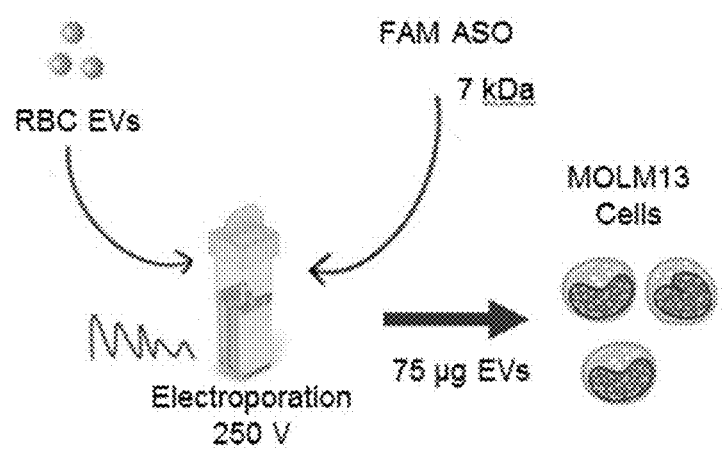
FIG. 5a is a schematic presentation of ASO delivery.
Figure 5B:
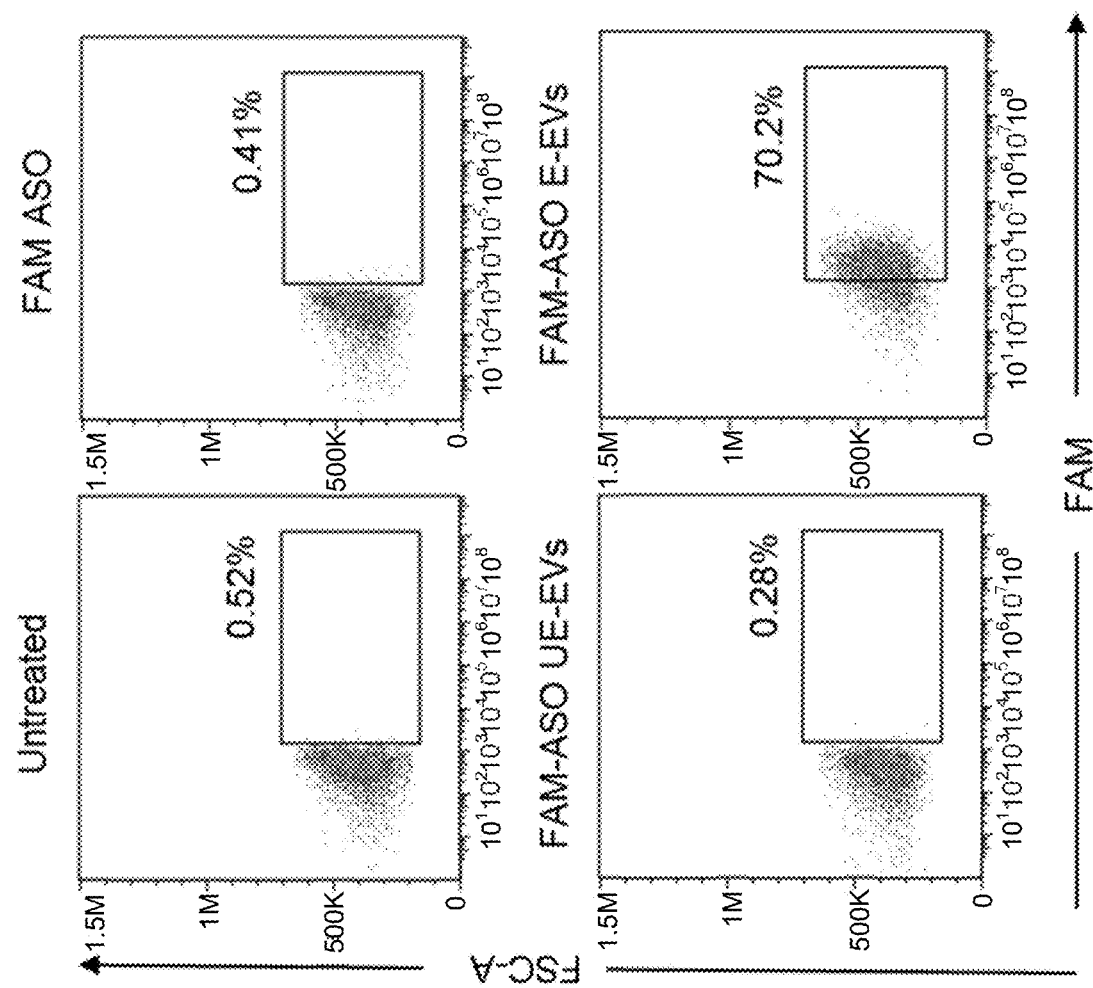
FIG. 5b shows the results obtained from FACS analysis, where the MOLM13 cells were untreated or incubated with FAM ASO or with electroporated EVs (E-EVs) or with unelectroporated EVs (UE-EVs).
Figure 5C:
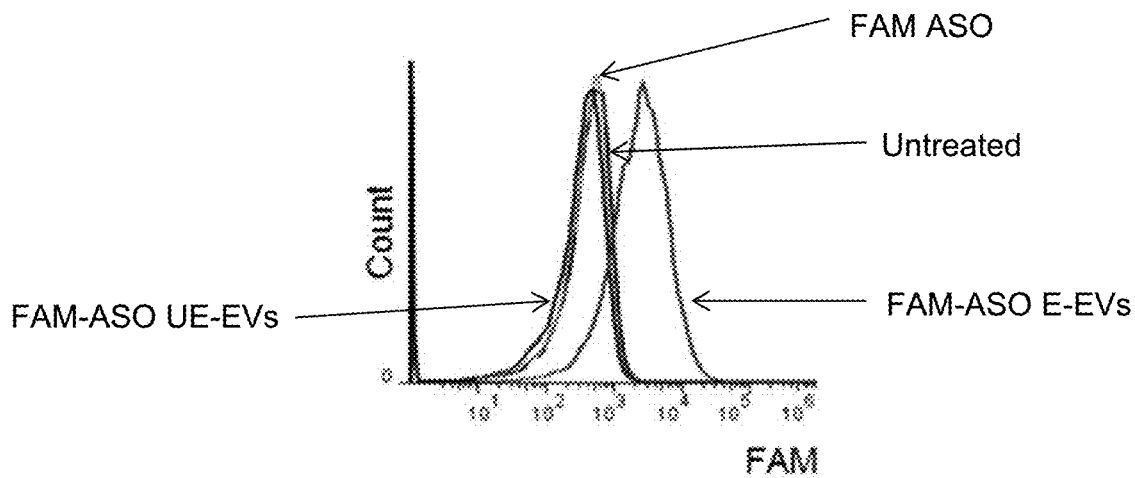
FIG. 5c is a plot showing the results of FIG. 5b.
Figure 5D:
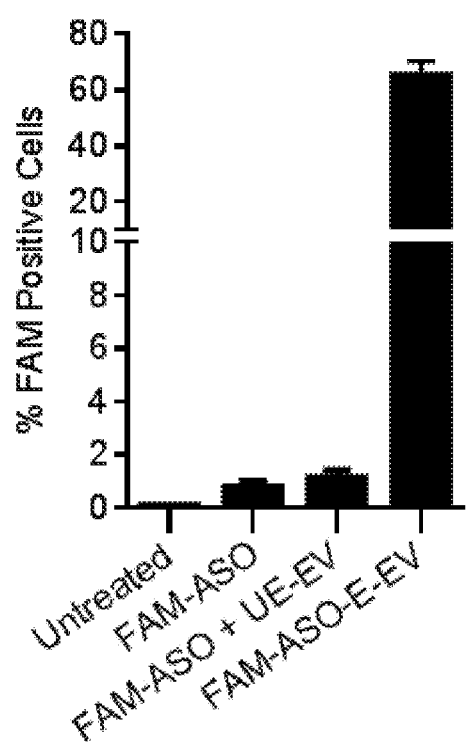
FIG. 5d is a diagram showing the average percentage of FAM-positive cells after treatments. In particular, the results reveal that RBC EVs deliver antisense oligonucleotides (ASO) to leukemia MOLM13 cells.

FIG. 5a: Schematic presentation of ASO delivery: 75 μg RBC EVs were electroporated with 400 pmole FAM fluorescent labeled scrambled ASO (~7 kDa) and incubated with MOLM13 cells for 24 hours. FIGS. 5b-5d: FACS analysis of FAM fluorescence in MOLM13 cells that were untreated or incubated with FAM ASO or with electroporated EVs (E-EVs) or with unelectroporated EVs (UE-EVs). The average percentage+SEM of FAM-positive cells were calculated from 3 independent experiments as shown in FIG. 5d.

The delivery of Dextran AF647 and FAM ASO by RBC EVs was then compared with that of two commercialized lipofection reagents, Lipofectamine™ 3000 (Thermo Fisher Scientific) and INTERFERin™ (Polyplus transfection) that are commonly used for transfection of nucleic acids in mammalian cells. Consistent with previous experiments, RBC EVs delivered Dextran AF647 and FAM ASO to ~75% MOLM13 cells. Lipofectamine™ 3000 archived only 3% and 55% delivery of Dextran AF647 and FAM ASO whereas INTERFERin archived only 2.7% and 38.7% delivery of Dextran AF647 and FAM ASO respectively in MOML13 cells. The poor delivery observed with Lipofectamine™ 3000 and INTERFERin was not a surprise since blood cells including AML cells are referred to as "difficult-to-transfect" cell types by the manufacturers. Hence, the 75% delivery efficiency archived by RBC EVs was a great improvement.

Figure 6A:
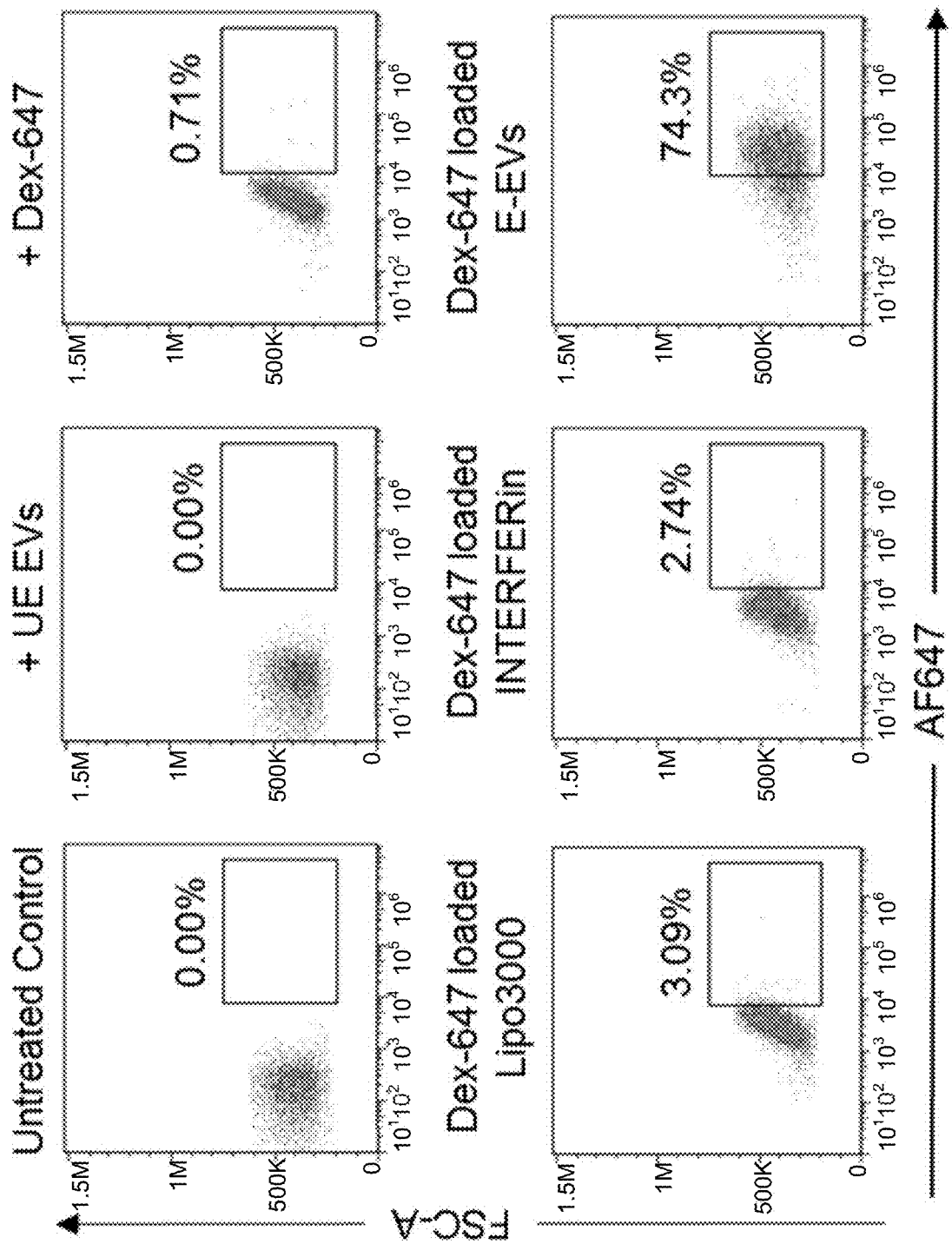
FIG. 6a shows the results obtained from FACS analysis of AF647 fluorescence in MOLM13 cells that were untreated, incubated with Dextran AF647 (Dex-647) alone, with Dex-647 and unelectroporated RBC EVs (UE-EVs), with Dex-647 loaded Lipofectamin™ 3000 (Lipo3000), with Dex-647 loaded INTERFERin or with Dex-647 electroporated RBC EVs (E-EVs) for 24 hours.
Figure 6B:
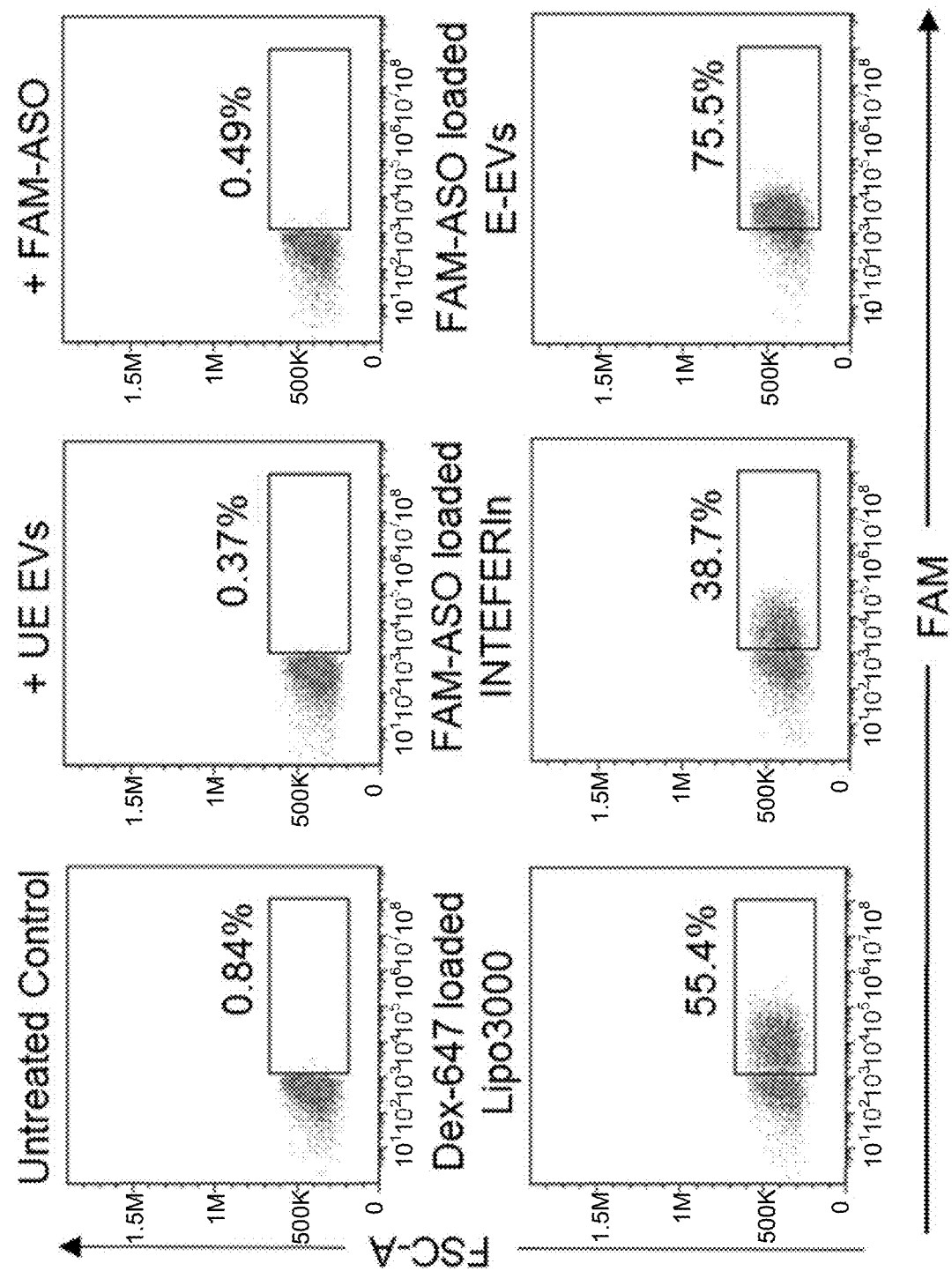
FIG. 6b shows the results obtained from FACS analysis of FAM fluorescence in MOLM13 cells that were untreated, incubated with FAM-ASO alone, with FAM-ASO and unelectroporated RBC EVs (UE-EVs), with FAM-ASO loaded Lipo3000, with FAM-ASO loaded INTERFERin or with FAM-ASO electroporated RBC EVs (E-EVs) for 24 hours.

FIG. 6a: FACS analysis of AF647 fluorescence in MOLM13 cells that were untreated, incubated with 4 μg Dextran AF647 (Dex-647) alone, with Dex-647 and unelectroporated RBC EVs (UE-EVs), with Dex-647 loaded Lipofectamin™ 3000 (Lipo3000), with Dex-647 loaded INTERFERin or with Dex-647 electroporated RBC EVs (E-EVs) for 24 hours. FIG. 6b: FACS analysis of FAM fluorescence in MOLM13 cells that were untreated, incubated with 2 μmole FAM-ASO alone, with FAM-ASO and unelectroporated RBC EVs (UE-EVs), with FAM-ASO loaded Lipo3000, with FAM-ASO loaded INTERFERin or with FAM-ASO electroporated RBC EVs (E-EVs) for 24 hours.

Moreover, RBC EVs exhibit no toxicity to the cells in contrast to about 20-30% increase in cell death caused by the transfection using Lipofectamine™ 3000 and INTERFERin.

Figure 7A:
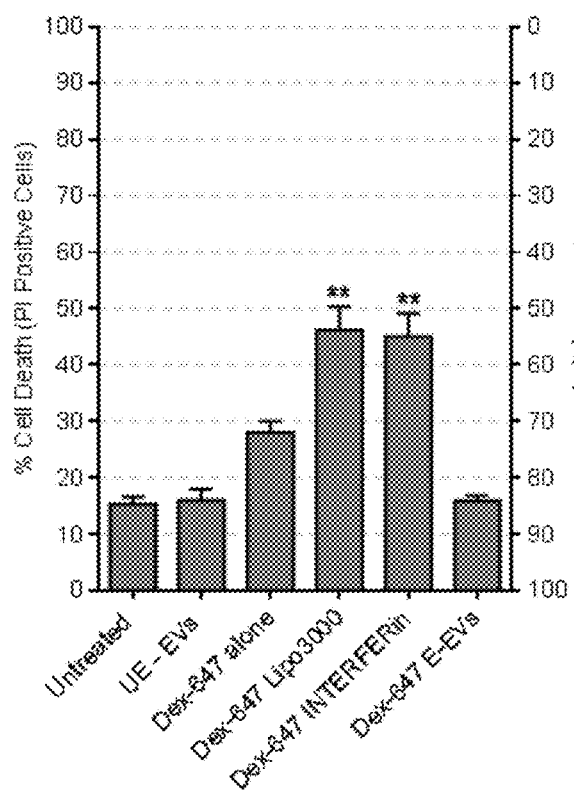
FIG. 7a shows the percentage of cell death/viability of MOLM13 cells after treatments with Dextran AF647 (Dex-647) alone, with Dex-647 and unelectroporated RBC EVs (UE-EVs), with Dex-647 loaded Lipofectamin™ 3000 (Lipo3000), with Dex-647 loaded INTERFERin or with Dex-647 electroporated RBC EVs (E-EVs) for 24 hours.
Figure 7B:
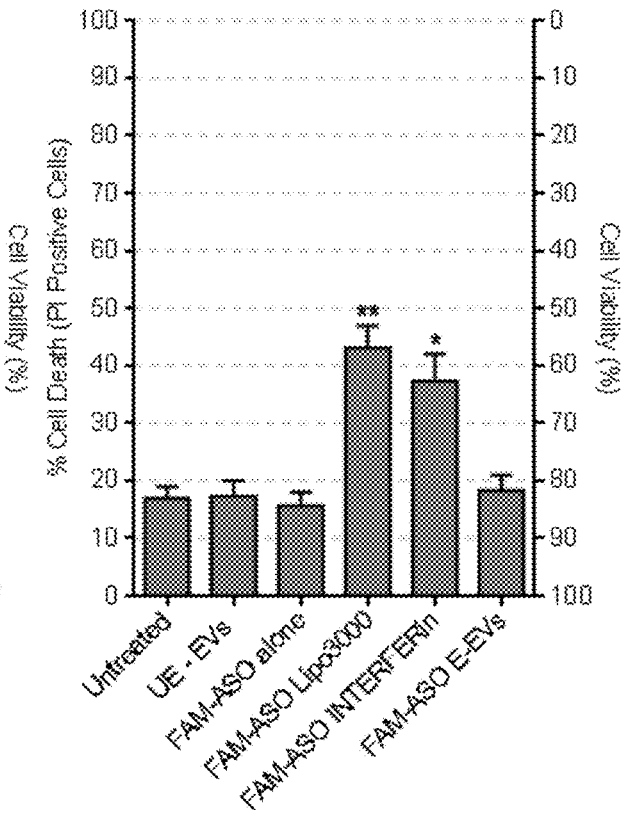
FIG. 7b shows the percentage of cell death/viability of MOLM13 cells after treatments with FAM-ASO alone, with FAM-ASO and unelectroporated RBC EVs (UE-EVs), with FAM-ASO loaded Lipo3000, with FAM-ASO loaded INTERFERin or with FAM-ASO electroporated RBC EVs (E-EVs) for 24 hours

The percentage of cell death was determined based on Propidium iodide (PI) staining and FACS analysis as shown in FIG. 7a: MOLM13 cells that were untreated, incubated with 4 μg Dextran AF647 (Dex-647) alone, with Dex-647 and unelectroporated RBC EVs (UE-EVs), with Dex-647 loaded Lipofectamin™ 3000 (Lipo3000), with Dex-647 loaded INTERFERin or with Dex-647 electroporated RBC EVs (E-EVs) for 24 hours; FIG. 7b: MOLM13 cells that were untreated, incubated with 2 µmole FAM-ASO alone, with FAM-ASO and unelectroporated RBC EVs (UE-EVs), with FAM-ASO loaded Lipo3000, with FAM-ASO loaded INTERFERin or with FAM-ASO electroporated RBC EVs (E-EVs) for 24 hours. The average cell death and SEM were calculated from three independent experiments. One-way Anova test: P<0.05; P<0.01.

The therapeutic potential of RBC EVs to deliver an ASO that antagonizes the oncogenic miR-125b in AML cells was further tested. miR-125b is upregulated in different types of cancer including AML and other leukemia. It has been shown that miR-125b suppresses apoptosis by regulating multiple genes in the p53 network. miR-125b also promotes proliferation of hematopoietic stem cells and leukemia cells in both humans and mouse models. An anti-miR-125b ASO (Shanghai Gene Pharma) comprising a sequence of SEQ ID NO: 1 was loaded into RBC EVs using electroporation and treated MOLM13 cells with these EVs. After 72 hours, it was found that the level of miR-125b was suppressed by 80-95% in a dose-dependent manner. miR-125a, the homologue of miR-125b, was also suppressed by 50-80% due to the sequence similarity to miR-125b. Inhibition of miR-125 led to a significant increase in BAK1, a target of miR-125a/b which regulates apoptosis. Treatment with miR-125b ASO loaded EVs also dampened the growth of MOLM13 cells significantly after 3-4 days of incubation. Hence, the inhibition of miR-125b using ASO in RBC EVs may represent a new approach for AML treatment.

As described here, miR-125b preferably comprises or consists of SEQ ID NO: 4 and miR-125a preferably comprises or consists of SEQ ID NO: 5. In particular, miR-125b consists of SEQ ID NO: 4 and miR-125a consists of SEQ ID NO: 5.

Figure 8A:
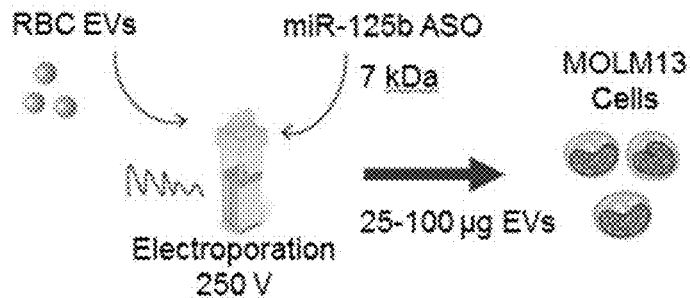
FIG. 8a is a schematic presentation of miR-125b ASO delivery.
Figure 8B:
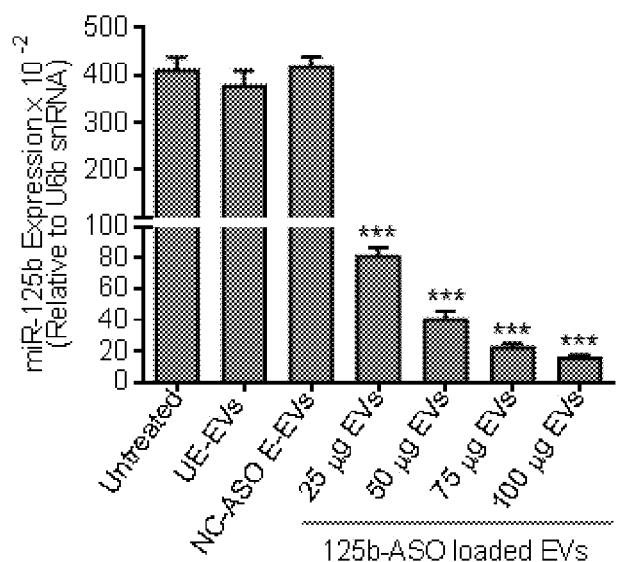
FIG. 8b shows the expression of miR-125b in MOLM13 cells after treatment with unelectroporated RBC EVs (UE-EVs), with negative control (NC)-ASO electroporated RBC EVs (E-EVs) or anti-miR-125b ASO (125b-ASO) electroporated RBC EVs for 72 hours.
Figure 8C:
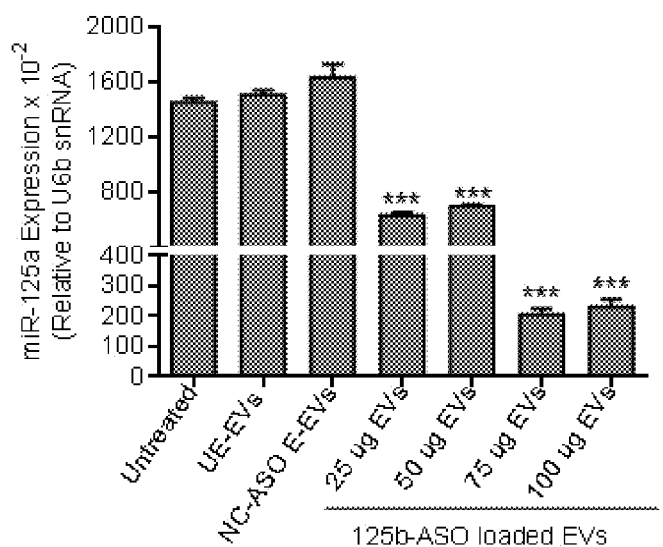
FIG. 8c shows the expression of miR-125a in MOLM13 cells after treatment with unelectroporated RBC EVs (UE-EVs), with negative control (NC)-ASO electroporated RBC EVs (E-EVs) or anti-miR-125b ASO (125b-ASO) electroporated RBC EVs for 72 hours.
Figure 8D:
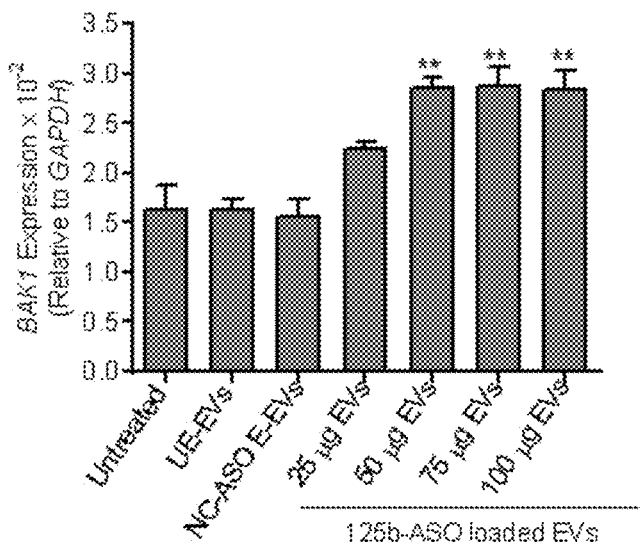
FIG. 8d shows the expression of BAK1 relative to GAPDH in MOLM13 cells treated the same as in FIGS. 8b and 8c.
Figure 8E:
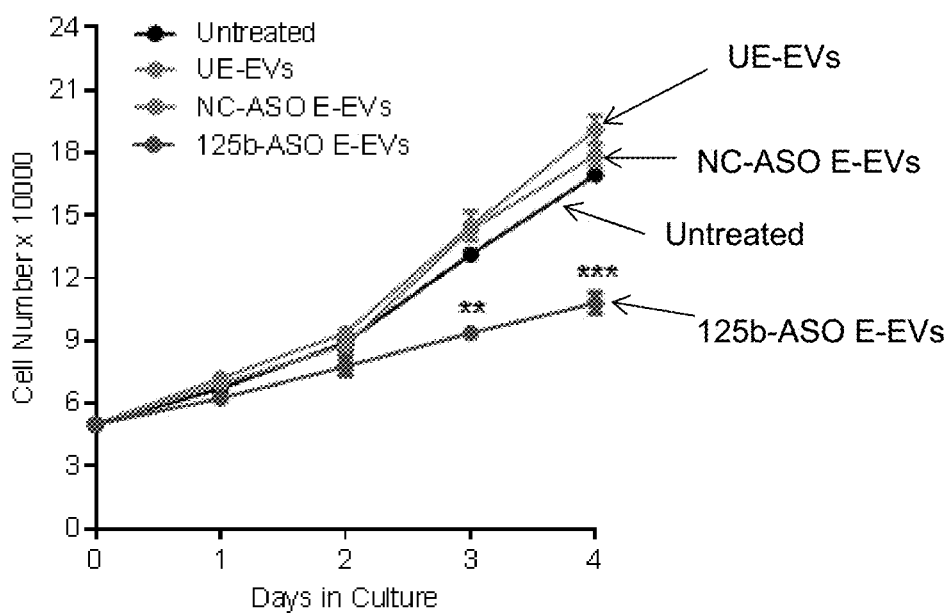
FIG. 8e shows the number of MOLM13 cells untreated, or treated with UE-EVs or with ASO electroporated EVs as indicated.

FIG. 8a: Schematic presentation of miR-125b ASO delivery: 25-100 µg RBC EVs were electroporated with 2 µmole anti-miR-125b ASO and incubated with MOLM13 cells. Anti-miR-125b ASO in this embodiment consists of SEQ ID NO: 1. FIGS. 8b-c: Expression of miR-125b and miR-125a relative to U6b snRNA in MOLM13 cells that were untreated, incubated with 100 ug unelectroporated RBC EVs (UE-EVs), with negative control (NC)-ASO electroporated RBC EVs (E-EVs) or anti-miR-125b ASO (125b-ASO) electroporated RBC EVs for 72 hours, as determined by Taqman qRT-PCR, presented as average and SEM. FIG. 8d: Expression of BAK1 relative to GAPDH in MOLM13 cells treated the same as in FIG. 8b. FIG. 8e: Number of MOLM13 cells untreated, or treated with UE-EVs or with ASO electroporated EVs as indicated. One-way Anova test: P<0.01; *P<0.001.

Similarly, RBC EVs were tested for the delivery of miR-125b ASO to breast cancer MCF10aCA1a (CA1a) cells. The inventors observed 80-90% knockdown of miR-125a and miR-125b in CA1a cells treated with miR-125b ASO loaded EVs. As a consequence, the knockdown of miR-125s suppressed the proliferation of CA1a cells.

Figure 9A:
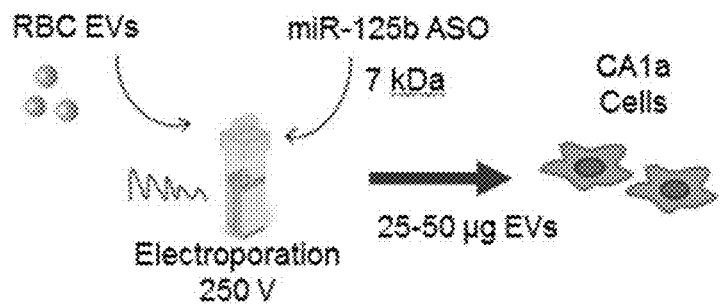
FIG. 9a is a schematic presentation of miR-125b ASO delivery.
Figure 9B:
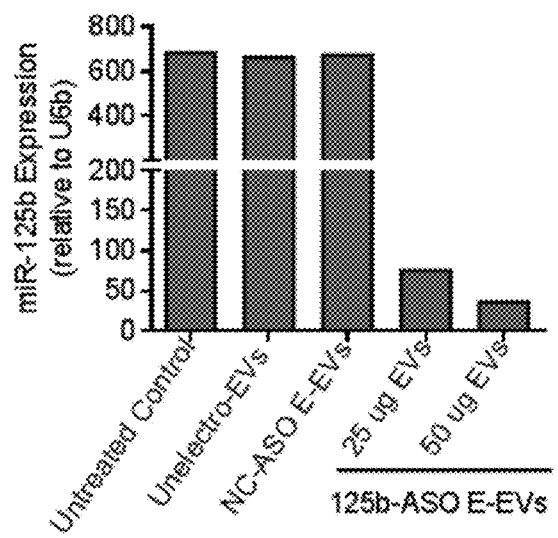
FIG. 9b shows the expression of miR-125b in CA1a cells after treatment with unelectroporated RBC EVs (UE-EVs), with negative control (NC)-ASO electroporated RBC EVs (E-EVs) or anti-miR-125b ASO (125b-ASO) electroporated RBC EVs for 72 hours.
Figure 9C:
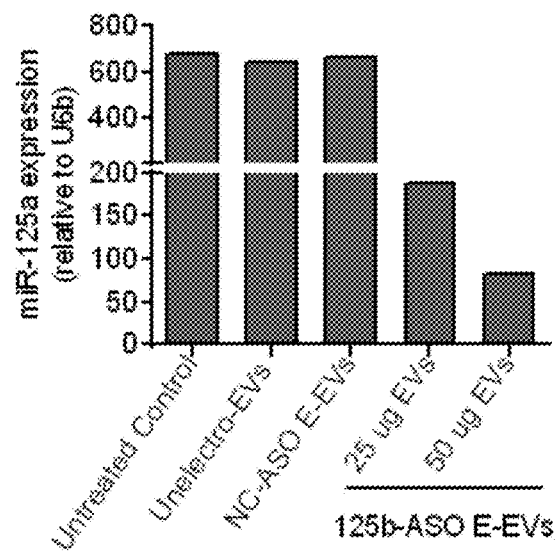
FIG. 9c shows the expression of miR-125a in CA1a cells after treatment with unelectroporated RBC EVs (UE-EVs), with negative control (NC)-ASO electroporated RBC EVs (E-EVs) or anti-miR-125b ASO (125b-ASO) electroporated RBC EVs for 72 hours.
Figure 9D:
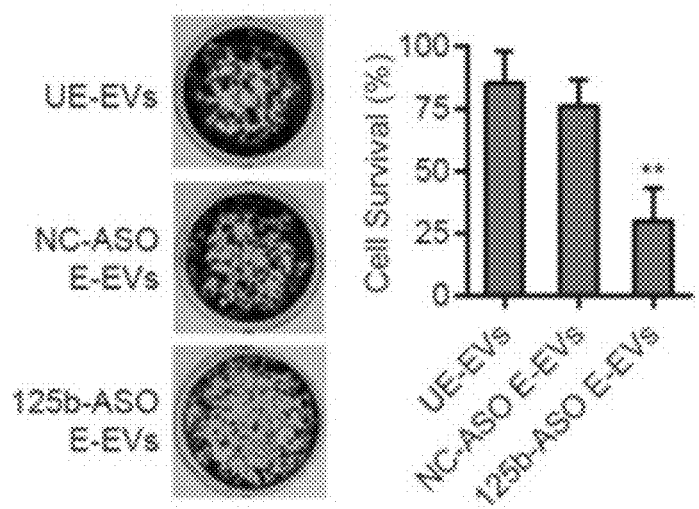
FIG. 9d shows the results of crystal violet staining of CA1a cells after treatments as indicated above.

FIG. 9a: Schematic presentation of miR-125b ASO delivery: 25-50 µg RBC EVs were electroporated with 2 µmole anti-miR-125b ASO and incubated with CA1a cells. FIG. 9b-c: Expression of miR-125b and miR-125a relative to U6b snRNA in CA1a cells that were untreated, incubated with unelectroporated RBC EVs (UE-EVs), with negative control (NC)-ASO electroporated RBC EVs (E-EVs) or anti-miR-125b ASO (125b-ASO) electroporated RBC EVs for 72 hours, as determined by Taqman qRT-PCR, presented as average and SEM. FIG. 9d: Crystal violet staining of CA1a cells untreated, or treated with UE-EVs or with ASO electroporated EVs as indicated. Bar graph represent the average number of cells counted in crystal-violet stained wells (n=3). One-way Anova test: **P<0.01.

To test the feasibility of CRISPR delivery using RBC EVs, synthetic SpCas9 mRNA (Trilink) was electroporated into RBC EVs using the protocol that was optimized for Dextran and ASO. As the result, a large amount of Cas9 mRNAs was detected in MOLM13 cells after a 24-hour incubation with the electroporated EVs, using qRT-PCR. Furthermore, using immunostaining of the HA-tag, Cas9 protein was found in the nuclei (overlapped with a nuclear stain) of ~50% MOLM13 cells at 48-hour post-treatment. This suggests that RBC EVs can be used to deliver the CRISPR Cas9 system.

Figure 10A:
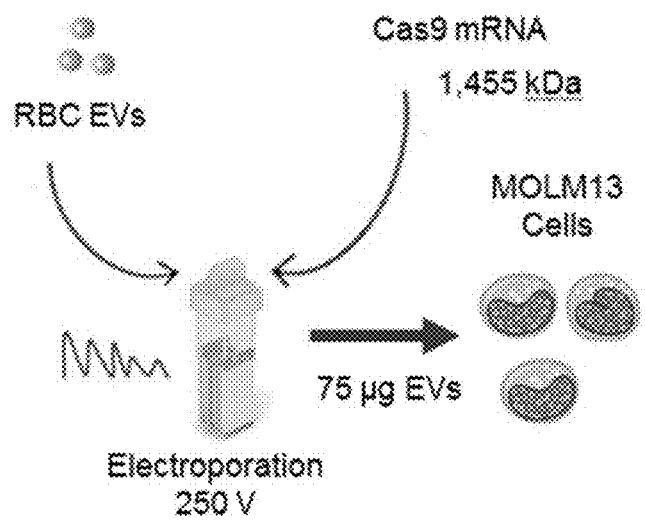
FIG. 10a is a schematic presentation of Cas9 mRNA delivery.
Figure 10B:
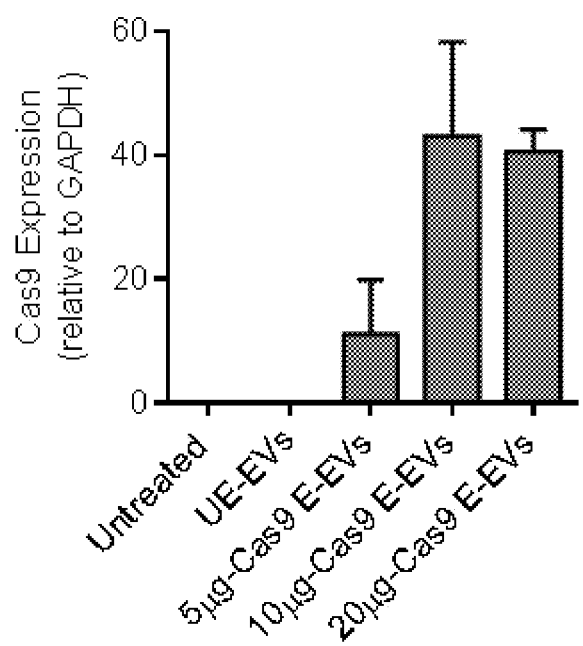
FIG. 10b shows the levels of Cas9 mRNA in MOLM13 cells after treatment with unelectroporated EVs or with EVs that were electroporated with 5, 10 or 20 µg Cas9 mRNA, determined by qRT-PCR after 24 hours of treatment.
Figure 10C:
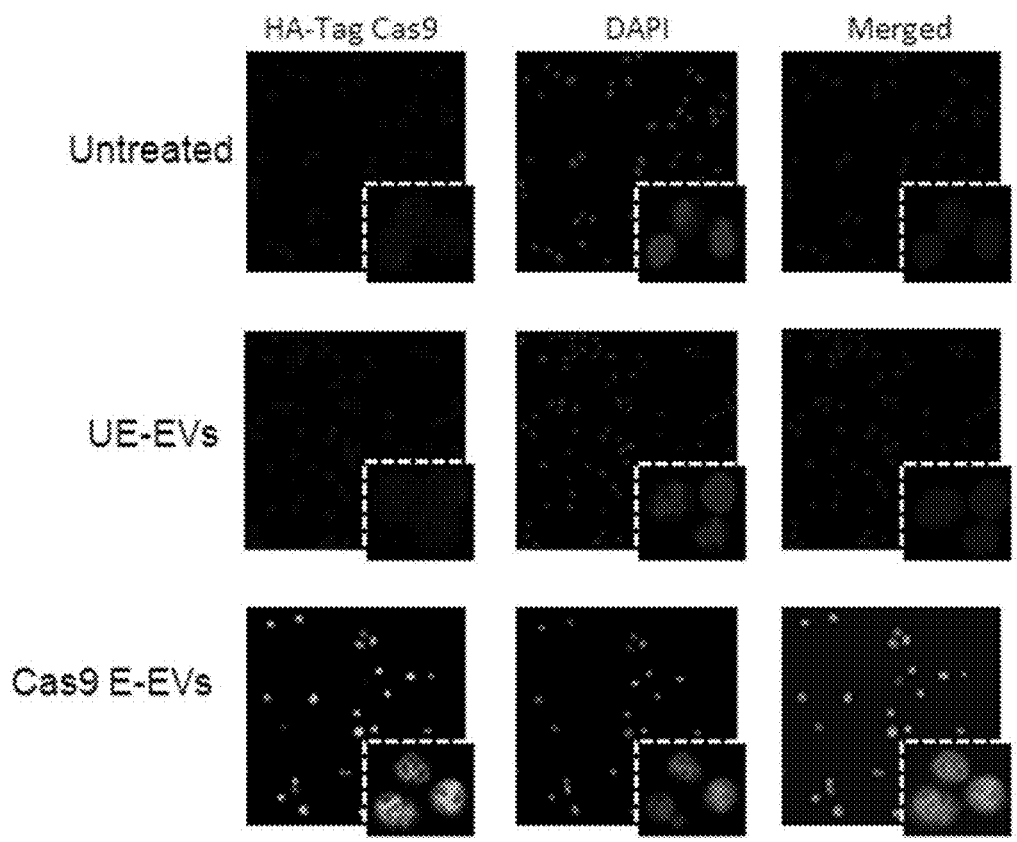
FIG. 10c show representative images of MOLM13 cells after treatments as indicated above.
Figure 10D:
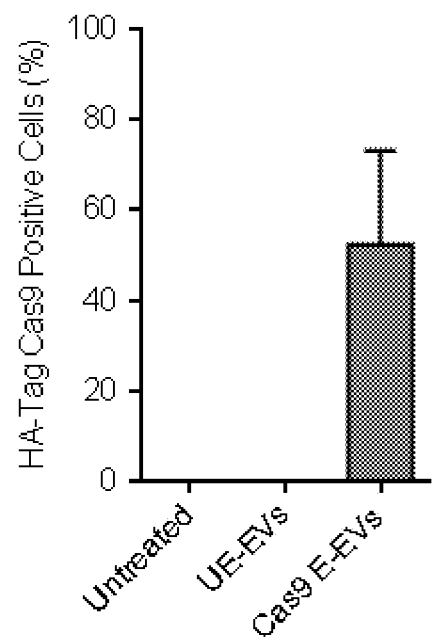
FIG. 10d shows the average percentage of MOLM13 cells stained positive for HA-Cas9 protein as shown in FIG. 10c.

FIG. 10a: Schematic presentation of Cas9 mRNA delivery: RBC EVs were electroporated with Cas9 mRNA and incubated with MOLM13 cells for 24 or 48 hours. FIG. 10b: The levels of Cas9 mRNA relative to GAPDH mRNA in MOLM13 cells that were untreated, incubated with unelectroporated EVs or with EVs that were electroporated with 5, 10 or 20 µg Cas9 mRNA, determined by qRT-PCR after 24 hours of treatment. Values are presented as mean±SEM (n=3). FIG. 10c: Representative images of MOLM13 cells that were untreated, or incubated for 48 hours with unelectroporated EVs or with EVs that were electroporated with 10 µg Cas9 mRNAs. The cells were stained for HA-Cas9 protein and nuclear DNA. FIG. 10d: Average percentage of MOLM13 cells stained positive for HA-Cas9 protein as shown in (c).

Subsequently, the inventors delivered Cas9 mRNA together with an anti-eGFP gRNA in RBC EVs to AML cells, NOMO1, that are labeled with eGFP. After one week, the inventors observed a complete knockout of eGFP in 32.9% NOMO1 cells. Hence, the RNAs delivered by RBC EVs were able to execute a CRISPR knockout of eGFP. As described herein, Cas9 mRNA preferably comprises or consists of SEQ ID NO: 2 and eGFP gRNA preferably comprises or consists of SEQ ID NO: 3. In particular, Cas9 mRNA consists of SEQ ID NO: 2 and eGFP gRNA consists of SEQ ID NO: 3.

Figure 11A:
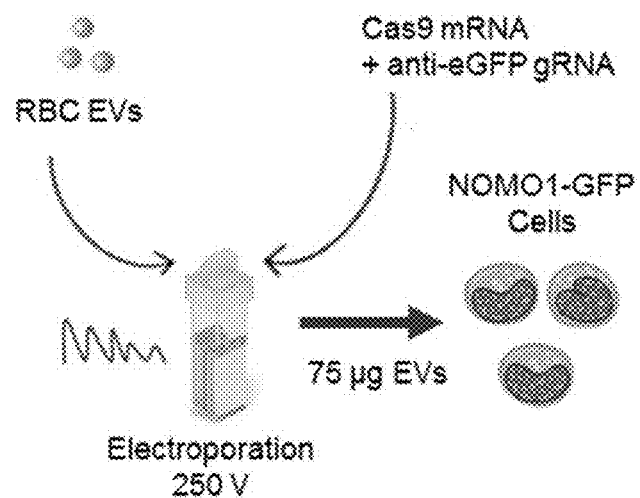
FIG. 11a is a schematic presentation of the RNA delivery.
Figure 11B:
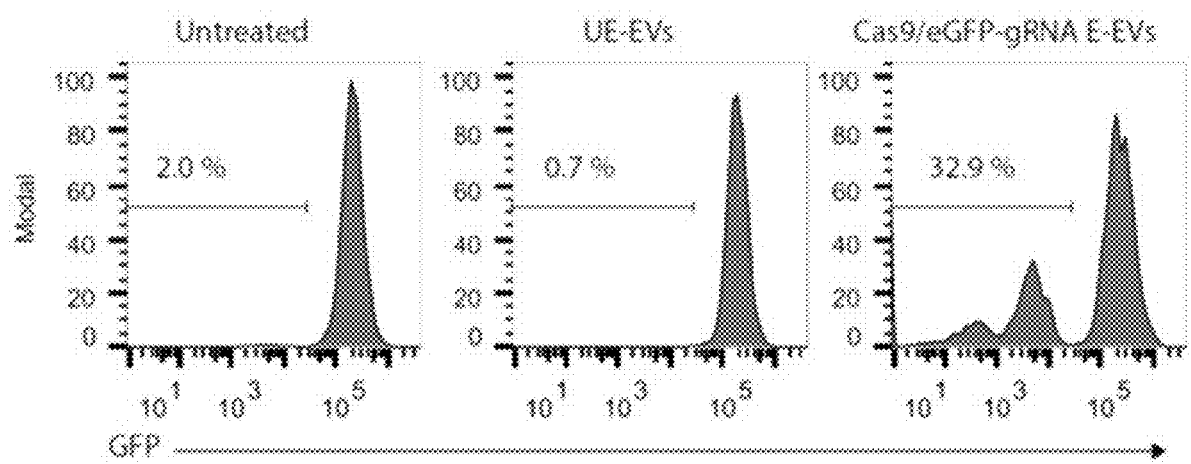
FIG. 11b shows the results obtained from FACS analysis of GFP in NOMO1-GFP cells after treatment with unelectroporated EVs or EVs electroporated with Cas9 and gRNA.

FIG. 11a: Schematic presentation of the RNA delivery: RBC EVs were electroporated with Cas9 mRNA and anti-GFP gRNA and incubated with NOMO1-GFP cells for 7 days. FIG. 11b: FACS analysis of GFP in NOMO1-GFP cells that were untreated, incubated with unelectroporated EVs or EVs electroporated with Cas9 and gRNA. The percentages of GFP-negative cells are shown above the gate.

In addition, the delivery of plasmids by RBC EVs was also tested. RBC EVs were electroporated with two plasmids, one expressing SpCas9 and one expressing gRNA against eGFP. Electroporated EVs were incubated with human embryonic kidney HEK-293T cells that homogenously express eGFP. After 96 hours, it was found that 13.8% GFP-negative cells resulted from the EV treatment, compared to 3.52% GFP-negative in the untreated population. Treatment with electroporated EVs showed a distinct peak of GFP-negative cells that suggests a homologous knockout of eGFP by the delivery of Cas9 and gRNA plasmids. Therefore, RBC EVs are able to deliver not only RNA but also plasmid DNA for genome editing. Moreover, the delivery is applicable to HEK-293T solid cancer cells.

Figure 12A:
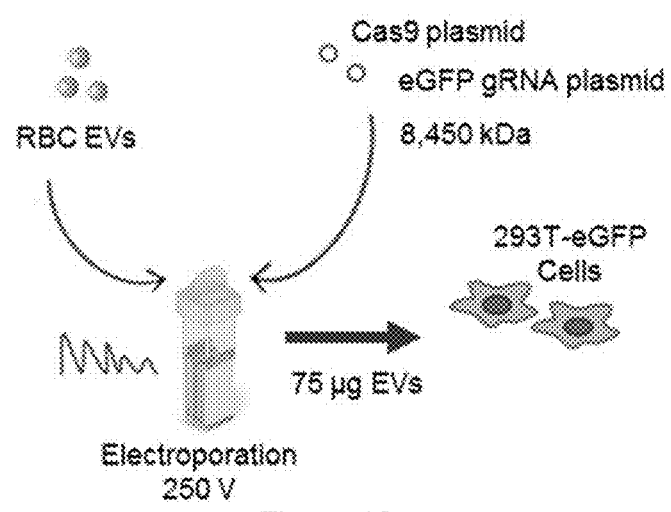
FIG. 12a is a schematic presentation of plasmid delivery.
Figure 12B:
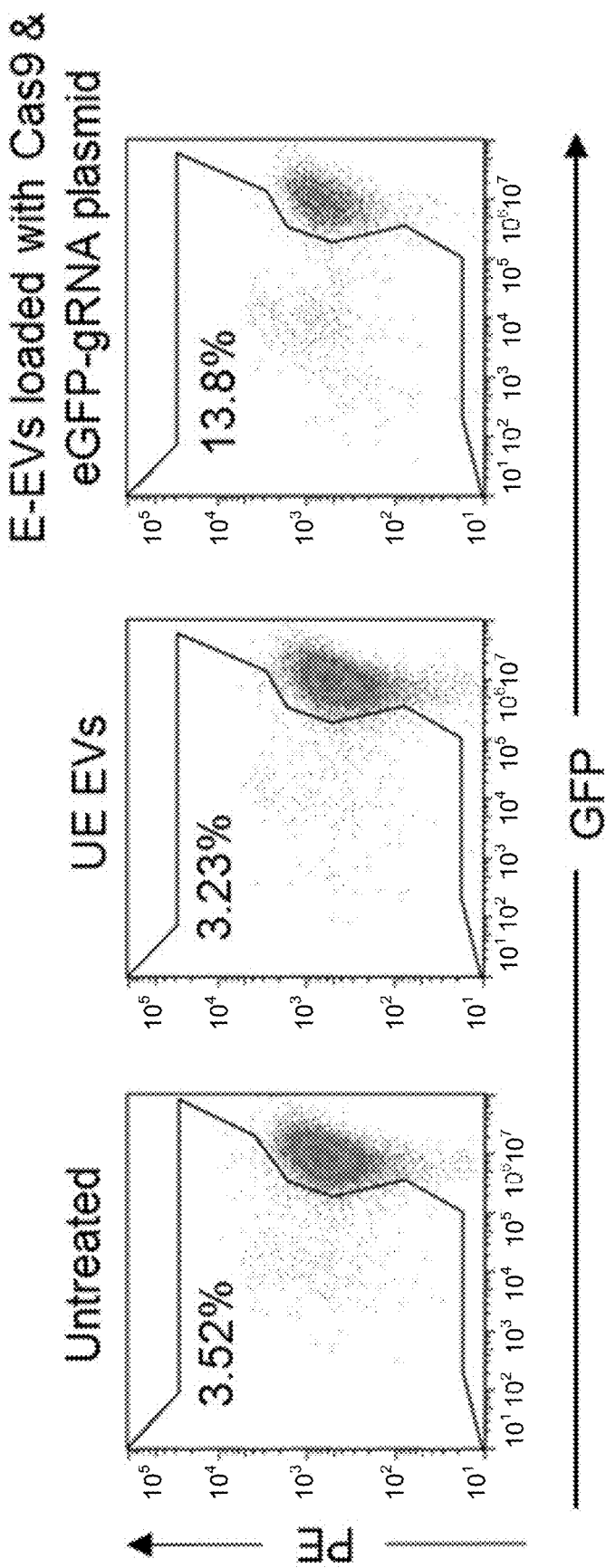
FIG. 12b shows the results obtained from FACS analysis of GFP in 293T-eGFP cells untreated, or incubated with unelectroporated EVs (UE-EVs) or with plasmid electroporated EVs (E-EVs) as indicated.
Figure 12C:
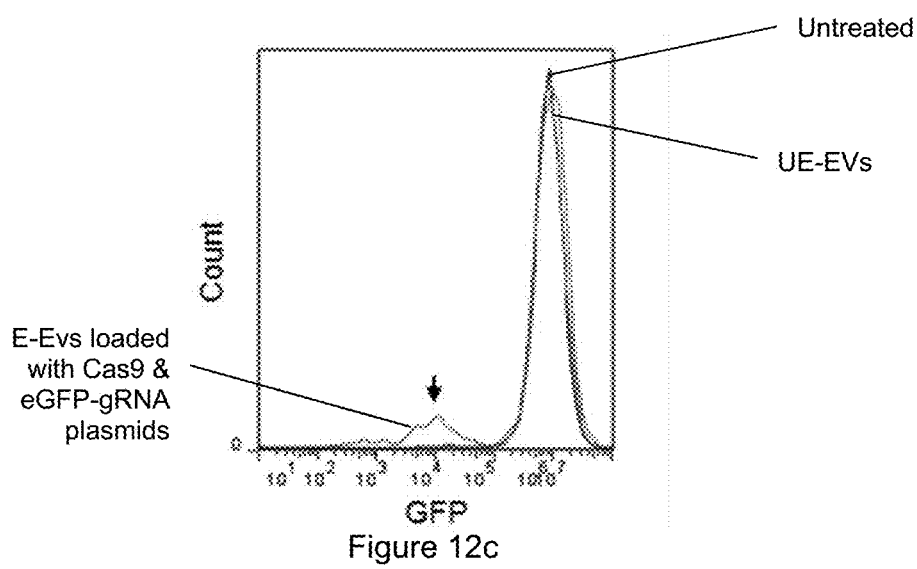
FIG. 12c shows the plot prepared from the results of FIG. 12b.

FIG. 12a Schematic presentation of plasmid delivery: RBC EVs were electroporated with Cas9 plasmid and eGFP gRNA plasmid and incubated with eGFP expressing 293T cells for 96 hours. FIGS. 12b-12c FACS analysis of GFP in 293T-eGFP cells untreated, or incubated with unelectroporated EVs (UE-EVs) or with plasmid electroporated EVs (E-EVs) as indicated. The GFP negative cells are indicated by the percentages in FIG. 12b and the arrow in FIG. 12c.

Figure 13A:
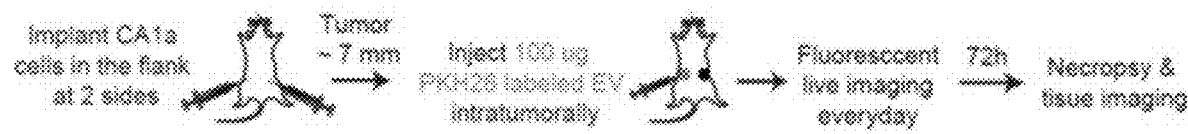
FIG. 13a is a schematic presentation of an in vivo EV uptake assay.
Figure 13B:
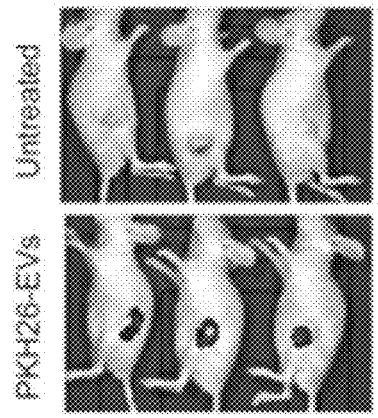
FIG. 13b shows the fluorescent images of nude mice bearing untreated tumors on the right and tumors injected with PKH26-labeled EVs on the left.
Figure 13C:
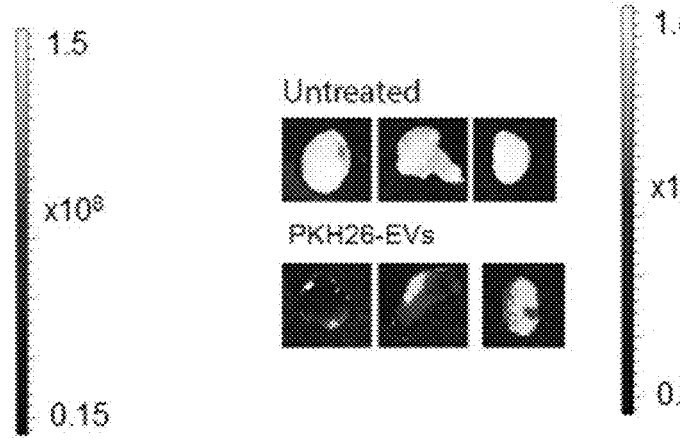
FIG. 13c shows the ex vivo fluorescent images of the tumors at 72 hours post-treatment.
Figure 13D:
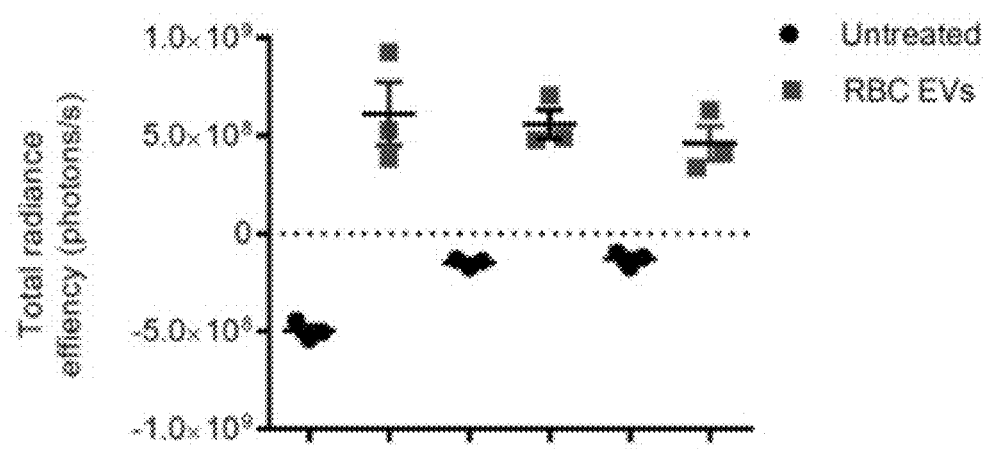
FIG. 13d shows the total radiance efficiency (photons/second) of fluorescent signals in the tumors 24-72 hours after the injection of PKH26-labeled EVs.

FIG. 13a: Schematic presentation of an in vivo EV uptake assay. FIG. 13b: Fluorescent images of nude mice bearing untreated tumors on the top and tumors injected with PKH26-labeled (red dye) EVs on the bottom. FIG. 13c: Ex vivo fluorescent images of the tumors at 72 hours post-treatment. FIG. 13d: Total radiance efficiency (photons/second) of fluorescent signals in the tumors 24-72 hours after the injection of PKH26-labeled EVs. To determine whether the RBC EVs are taken up by tumor cells in vivo, CA1a cells were implanted in the mice, in the flank at 2 sides (FIG. 13a). The tumor size is about 7 mm. 100 µg of PKH26 labelled EVs were then injected intratumorally. Fluorescent live imaging was done every day for 3 days (72 hours). Images of nude mice bearing untreated tumors and tumors injected with PKH26-labeled (red dye) EVs were taken (FIG. 13b). With reference to FIG. 13c, it shows ex vivo fluorescent images of the tumors at 72 hours post-treatment and proves that PKH26-labeled EVs were taken up by tumor cells. The total radiance efficiency (photons/second) of fluorescent signals in the tumors decreased gradually 24 to 72 hours after the injection of PKH26-labeled EVs as shown in FIG. 13d.

It will be appreciated by persons skilled in the art that numerous variations and/or modifications may be made to the present invention as shown in the specific embodiments without departing from the spirit or scope of the invention as broadly described. The present embodiments are, therefore, to be considered in all respects as illustrative and not restrictive.

It will also be appreciated by persons skilled in the art that the present invention may also include further additional modifications made to the method which does not affect the overall functioning of the method.

Any reference to prior art contained herein is not to be taken as an admission that the information is common general knowledge, unless otherwise indicated. It is to be understood that, if any prior art information is referred to herein, such reference does not constitute an admission that the information forms a part of the common general knowledge in the art, any other country.

The invention claimed is:

1. A method for RNA delivery to leukemic or breast cancer target cells comprising:
   a) purification of extracellular vesicles (EVs) from red blood cells (RBCs) using ultracentrifugation with a sucrose cushion, wherein the RBCs have been treated overnight with calcium ionophore;
   b) electroporation of the EVs with RNAs to form RNA-loaded EVs; and
   c) applying the RNA-loaded EVs to the target cells.

2. The method of claim 1, wherein the RBCs are derived from a human.

3. The method of claim 1, wherein the RNAs comprise antisense oligonucleotides (ASO) and mRNAs.

4. The method of claim 1, wherein the target cells comprise cancer cells.

5. The method of claim 1, wherein the target cells comprise acute myeloid leukemia (AML) cells, breast cancer cells, or a combination of AML cells and breast cancer cells.

6. The method of claim 1, wherein the EVs are electroporated with ASO antagonizing miR-125b.

7. The method of claim 1, wherein the growth of the target cells is suppressed.

8. The method of claim 1, wherein the EVs are electroporated with dextran.

9. The method of claim 1, comprising administering to the target cells the RNA-loaded EVs which modulate an apoptosis-related gene expression, thereby inducing apoptosis in the target cells.

10. A method for delivery of an antisense oligonucleotide (ASO) to leukemic or breast cancer target cells to suppress gene expression, wherein the method comprises:
   a) purification of extracellular vesicles (EVs) from red blood cells (RBCs) using ultracentrifugation with a sucrose cushion, wherein the RBCs have been treated overnight with calcium ionophore;
   b) electroporation of the EVs with ASOs to form ASO-loaded EVs; and
   c) applying the ASO-loaded EVs to the target cells.

11. The method of claim 10, wherein the RBCs are derived from a human.

12. The method of claim 10, wherein the RNA is an ASO antagonizing miR-125b to inhibit the oncogenic miR-125b in the target cells.

13. The method of claim 10, wherein the target cells are acute myeloid leukemia (AML) cells, breast cancer cells, or a combination of AML cells and breast cancer cells.

14. A method for RNA delivery to leukemic or breast cancer target cells for a CRISPR genome editing system comprising:
   a) purification of extracellular vesicles (EVs) from red blood cells (RBCs) using ultracentrifugation with a sucrose cushion, wherein the RBCs have been treated overnight with calcium ionophore;
   b) electroporation of the EVs with RNAs to form RNA-loaded EVs; and
   c) applying the RNA-loaded EVs to the target cells.

15. The method of claim 14, wherein the EVs are electroporated with Cas9 mRNA and guide RNA.

16. The method of claim 14, wherein the EVs are electroporated with Cas9 and gRNA plasmids.

17. The method of claim 14, wherein the target cells are cancer cells.

18. The method of claim 14, wherein the target cells are leukemia cells.

19. A method of treating cancer by delivery of RNA to leukemic or breast cancer target cells comprising:
   a) purification of extracellular vesicles (EVs) from red blood cells (RBCs) using ultracentrifugation with a sucrose cushion, wherein the RBCs have been treated overnight with calcium ionophore;
   b) electroporation of the EVs with RNAs to form RNA-loaded EVs; and
   c) applying the RNA-loaded EVs to the target cells thereby inhibiting the growth of the target cells, wherein the target cells comprise cancer cells.

20. The method of claim 19, wherein the target cells comprises leukemia cells, breast cancer cells, or a combination of leukemia cells and breast cancer cells.

21. The method of claim 19, wherein the target cells comprise acute myeloid leukemia cells.

22. The method of claim 19, wherein the step c) comprises a step of administering the RNA-loaded EVs to a subject having the target cells via a local or systemic administration.

23. The method of claim 19, wherein the growth of the target cells is suppressed after the step c).

24. A method for RNA delivery to leukemic or breast cancer target cells comprising:
   a) purification of extracellular vesicles (EVs) from red blood cells (RBCs) using ultracentrifugation with a sucrose cushion, wherein the RBCs have been treated with 10 mM calcium ionophore;
   b) electroporation of the EVs with RNAs to form RNA-loaded EVs; and
   c) applying the RNA-loaded EVs to the target cells.

* * * * *

SEQUENCE LISTING

```
<160> NUMBER OF SEQ ID NOS: 5

<210> SEQ ID NO 1
<211> LENGTH: 22
<212> TYPE: RNA
<213> ORGANISM: Artificial Sequence
<220> FEATURE:
<223> OTHER INFORMATION: Synthesized

<400> SEQUENCE: 1
ucacaaguua gggucucagg ga                                             22

<210> SEQ ID NO 2
<211> LENGTH: 4107
<212> TYPE: RNA
<213> ORGANISM: Artificial Sequence
<220> FEATURE:
<223> OTHER INFORMATION: Synthesized

<400> SEQUENCE: 2
auggauaaga aauacucaau aggcuuagau aucggcacaa auagcgucgg augggcggug      60
aucacugaug aauauaaggu uccgucuaaa aaguucaagg uucugggaaa uacagaccgc     120
cacaguauca aaaaaaaucu uauaggggcu cuuuuauuug acaguggaga gacagcggaa     180
gcgacucguc ucaaacggac agcucguaga agguauacac gucggaagaa ucguauuugu     240
uaucuacagg agauuuuuuc aaaugagaug gcgaaaguag augauaguuu cuuucaucga     300
cuugaagagu cuuuuuggu ggaagaagac aagaagcaug aacgucaucc uauuuuugga     360
aauauaguag augaaguugc uuaucaugag aaauauccaa cuaucuauca ucugcgaaaa     420
aaauggguag auucuacuga uaaagcggau uugcgcuuaa ucuauuuggc cuagcgcau      480 augauuaagu uucgugguca uuuuuugauu gagggagauu uaauccuga uaauagugau     540 guggacaaac uauuuaucca guugguacaa accuacaauc aauuauuuga agaaaacccu     600
auuaacgcaa guggaguaga ugcuaaagcg auucuuucug cacgauugag uaaaucaaga     660
cgauuagaaa aucucauugc ucagcucccc ggugagaaga aaaauggcuu auuugggaau     720
cucauugcuu ugucauuggg uuugacccu aauuuuaaau caaauuuuga uuggcagaaa     780
gaugcuaaau uacagcuuuc aaaagauacu uacgaugaug auuuagauaa uuuauggcg     840
```

```
caaauuggag aucaauaugc ugauuuguuu uuggcagcua agaauuuauc agaugcuauu    900
uuacuuucag auauccuaag aguaaauacu gaaauaacua aggcucccu aucagcuuca    960 augauuaaac gcuacgauga acaucaucaa gacuugacuc uuuuaaaagc uuuaguucga   1020
caacaacuuc cagaaaagua uaagaaauc uuuuugauc aaucaaaaaa cggauaugca   1080
gguuauauug augggggagc uagccaagaa gaauuuaua aauuuaucaa accaauuuua   1140
gaaaaaaugg augguacuga ggaauuauug gugaaacuaa aucgugaaga uuugcugcgc   1200
aagcaacgga ccuuugacaa cggcucuauu ccccaucaaa uucacuuggg ugagcugcau   1260
gcuauuuuga gaagacaaga agacuuuau ccauuuuuaa aagacaaucg ugagaagauu   1320
gaaaaaaucu ugacuuuucg aauuccuuau uauguuuguc cauuggcgcg uggcaauagu   1380
cguuuugcau ggaugacucg gaagucugaa gaaacaauua ccccauggaa uuuugaagaa   1440
guugucgaua aaggugcuuc agcucaauca uuuauugaac gcaugacaaa cuuugauaaa   1500
aaucuuccaa augaaaaagu acuaccaaaa cauaguuugc uuuauagua uuuuacgguu   1560 uauaacgaau ugacaaaggu caaauauguu acugaaggaa ugcgaaaacc agcauuucuu   1620
ucaggugaac agaagaaagc cauuguugau uuacucuuca aaacaaaucg aaaaguaacc   1680
guuaagcaau uaaagaaga uuauuucaaa aaaauagaau guuuugauag guugaaauu   1740 ucaggaguug aagauagauu uaaugcuuca uuagguaccu accaugauuu gcuaaaaauu   1800
auuaagauaa aagauuuuuu ggauaaugaa gaaaaugaag auaucuuaga ggauauuguu   1860
uuaacauuga ccuuauuuga agauaggag augauugagg aaagacuuaa aacauaugcu   1920
caccucuuug augauaaggu gaugaaacag cuuaaacguc gccguauac ugguuggga   1980 cguuugucuc gaaaauugau uaauggauau agggauaagc aaucggcaa aacaauauua   2040 gauuuuuuga aaucagaugg uuuugccaau cgcaauuuua ugcagcugau ccaugaugau   2100
aguuugacau uuaagaaga cauucaaaaa gcacaagugu cuggacaagg cgauaguuua   2160
caugaacaua uugcaaauuu agcugguagc ccugcuauua aaaaagguau uuacagacu   2220 guaaaaguug uugaugaauu ggucaaagua augggcggc auaagccaga aaauaucguu   2280
auugaaaugg cacgugaaaa ucagacaacu caaaagggcc agaaaaauuc gcgagagcgu   2340
augaaacgaa ucgaagaagg uaucaaagaa uuaggaaguc agauucuuaa agagcauccu   2400
guugaaaaua cucaauugca aaaugaaaag cucuaucucu auuaucucca aaauggaaga   2460
gacauguaug uggaccaaga auuagauauu aaucguuuaa gugauuauga ugucgaucac   2520
auuguuccac aaaguuuccu uaagacgau ucaauagaca auaaggucuu aacgcguucu   2580
gauaaaaauc gugguaaauc ggauacguu ccaagugaag aaguagucaa aaagaugaaa   2640
aacuauugga gacaacuucu aaacgccaag uuaaucacuc aacguaaguu ugauaauuua   2700
acgaaagcug aacguggagg uuugagugaa cuugauaaag cugguuuau caaacgccaa   2760 uugguugaaa cucgccaaau cacuaagcau guggcacaaa uuuuggauag ucgcaugaau   2820
acuaaauacg augaaaauga uaaacuuauu cgagagguua agugauuac cuuaaaaucu   2880 aaauuaguuu cugacuuccg aaaagauuuc caauucuaua aaguacguga gauuaacaau   2940
uaccaucaug cccaugaugc guaucuaaau gccgucguug aacugcuuu gauuaagaaa   3000 uauccaaaac uugaaucgga guuugucuau ggugauuaua aguuuauga uguucguaaa   3060 augauugcua agucugagca agaaauaggc aaagcaaccg caaaauauuu cuuuuacucu   3120
aauaucauga acuucuucaa aacagaaauu acacuugcaa auggagagau ucgcaaacgc   3180
```

```
ccucuaaucg aaacuaaugg ggaaacugga gaaauugucu gggauaaagg gcgagauuuu    3240
gccacagugc gcaaaguauu guccaugccc caagucaaua uugucaagaa aacagaagua    3300
cagacaggcg gauucuccaa ggagucaauu uuaccaaaaa gaaauucgga caagcuuauu    3360
gcucguaaaa aagacuggga uccaaaaaaa uauggugguu uugauagucc aacgguagcu    3420
uauucagucc uagugguugc uaagguggaa aaagggaaau cgaagaaguu aaaauccguu    3480
aaagaguuac uagggaucac aauuauggaa agaaguuccu uugaaaaaaa uccgauugac    3540
uuuuuagaag cuaaggaua uaaggaaguu aaaaaagacu uaaucauuaa acuaccuaaa     3600
uauagucuuu uugaguuaga aaacggucgu aaacggaugc uggcuagugc cggagaauua    3660 caaaaggaa augagcuggc ucugccaagc aaauauguga auuuuuaua uuuagcuagu      3720 cauuaugaaa aguugaaggg uaguccagaa gauaacgaac aaaaacaauu guuuguggag    3780
cagcauaagc auuauuuaga ugagauuauu gagcaaauca gugaauuuuc uaagcguguu    3840
auuuuagcag augccaauuu agauaaaguu cuuagugcau auaacaaaca uagagacaaa    3900
ccaauacgug aacaagcaga aaauauuauu cauuuauuua cguugacgaa ucuuggagcu    3960
cccgcugcuu uuaaauauuu ugauacaaca auugaucgua aacgauauac gucuacaaaa    4020
gaaguuuuag augccacucu uauccaucaa uccaucacug gucuuuauga aacacgcauu    4080
gauuugaguc agcuaggagg ugacuga                                       4107

<210> SEQ ID NO 3
<211> LENGTH: 20
<212> TYPE: RNA
<213> ORGANISM: Artificial Sequence
<220> FEATURE:
<223> OTHER INFORMATION: Synthesized

<400> SEQUENCE: 3
gggcacgggc agcuugccgg                                                 20

<210> SEQ ID NO 4
<211> LENGTH: 22
<212> TYPE: RNA
<213> ORGANISM: Homo sapiens

<400> SEQUENCE: 4
ucccugagac ccuaacuugu ga                                              22

<210> SEQ ID NO 5
<211> LENGTH: 24
<212> TYPE: RNA
<213> ORGANISM: Homo sapiens

<400> SEQUENCE: 5
ucccugagac ccuuuaaccu guga                                            24
```